(12) United States Patent
Lee

(10) Patent No.: US 11,390,836 B2
(45) Date of Patent: Jul. 19, 2022

(54) CHIP PLATFORMS FOR MICROARRAY 3D BIOPRINTING

(71) Applicant: Cleveland State University, Cleveland, OH (US)

(72) Inventor: Moo-Yeal Lee, Pepper Pike, OH (US)

(73) Assignee: Cleveland State University, Cleveland, OH (US)

( * ) Notice: Subject to any disclaimer, the term of this patent is extended or adjusted under 35 U.S.C. 154(b) by 1221 days.

(21) Appl. No.: 15/816,485

(22) Filed: Nov. 17, 2017

(65) Prior Publication Data

US 2018/0142195 A1    May 24, 2018

Related U.S. Application Data

(60) Provisional application No. 62/423,586, filed on Nov. 17, 2016.

(51) Int. Cl.
*C12M 3/00* (2006.01)
*C12M 1/12* (2006.01)
(Continued)

(52) U.S. Cl.
CPC ............ *C12M 21/08* (2013.01); *B33Y 10/00* (2014.12); *B33Y 30/00* (2014.12); *B33Y 70/00* (2014.12); *B33Y 80/00* (2014.12); *C12M 23/12* (2013.01); *C12M 23/34* (2013.01); *C12M 25/04* (2013.01); *C12M 29/10* (2013.01); *C12N 5/0062* (2013.01);
(Continued)

(58) Field of Classification Search
CPC ...... C12M 21/08; C12M 23/12; C12M 23/34; C12M 25/04; C12M 29/10; C12M 33/00; B33Y 30/00; B33Y 10/00; B33Y 70/00; B33Y 80/00; C12N 5/0062; G01N 33/5014; G01N 33/5026; G01N 33/00
See application file for complete search history.

(56) References Cited

U.S. PATENT DOCUMENTS 4,871,647 A    10/1989  Komamura et al.
6,022,700 A     2/2000  Monks
(Continued)

FOREIGN PATENT DOCUMENTS

CA    2398271 A1    8/2001
CN    101218028 A   7/2008
(Continued)

OTHER PUBLICATIONS

European Partial Search Report and Provisional Opinion for EP Appln. No. 17871475.4 dated May 29, 2020.
(Continued)

*Primary Examiner* — Michael L Hobbs
(74) *Attorney, Agent, or Firm* — Calfee, Halter & Griswold LLP

(57) ABSTRACT

A micropillar and microwell chip and methods of studying cellular environments using micropillar and microwell chips is disclosed. The micropillar chip may include at least one micropillar with a pillar-microwell. The microwell chip may include at least one microwell with an upper and a lower microwell. A perfusion channel chip that may be integrated with a micropillar chip is also disclosed. The perfusion channel chip may include a channel, a pillar-insertion hole, a membrane cassette, and a reservoir well.

15 Claims, 23 Drawing Sheets

(51) Int. Cl.
  *G01N 33/50* (2006.01)
  *C12M 1/00* (2006.01)
  *C12M 1/32* (2006.01)
  *B33Y 30/00* (2015.01)
  *B33Y 10/00* (2015.01)
  *B33Y 70/00* (2020.01)
  *B33Y 80/00* (2015.01)
  *C12N 5/00* (2006.01)

(52) U.S. Cl.
  CPC ..... *G01N 33/5014* (2013.01); *G01N 33/5026* (2013.01)

(56) References Cited

U.S. PATENT DOCUMENTS

| | | | |
|---|---|---|---|
| 7,148,058 B2 | 12/2006 | Charych | |
| 7,332,328 B2 | 2/2008 | Webb et al. | |
| 8,778,849 B2 | 7/2014 | Bowen et al. | |
| 9,097,702 B2 | 8/2015 | Fischbach | |
| 9,133,429 B2 | 9/2015 | Higuera et al. | |
| 9,481,868 B2 | 11/2016 | Nguyen et al. | |
| 9,758,533 B2 | 9/2017 | Tuttle | |
| 10,605,708 B2 | 3/2020 | Shao | |
| 2003/0124029 A1* | 7/2003 | Webb | B01L 3/50853 435/287.2 |
| 2004/0197236 A1 | 10/2004 | Vanmaele | |
| 2008/0103059 A1 | 5/2008 | Webb | |
| 2009/0263849 A1 | 10/2009 | Sun et al. | |
| 2011/0152128 A1 | 6/2011 | Herrmann et al. | |
| 2011/0190162 A1 | 8/2011 | Lee et al. | |
| 2011/0212501 A1 | 9/2011 | Yoo | |
| 2011/0259742 A1 | 10/2011 | Li | |
| 2012/0088693 A1* | 4/2012 | Lee | C12M 23/12 506/15 |
| 2012/0135890 A1 | 5/2012 | Shin | |
| 2012/0165224 A1 | 6/2012 | Song et al. | |
| 2012/0183636 A1 | 7/2012 | Kim et al. | |
| 2013/0081483 A1* | 4/2013 | Jeong | B01L 3/5088 73/864.91 |
| 2014/0045256 A1 | 2/2014 | Lee et al. | |
| 2014/0141503 A1 | 5/2014 | Hong et al. | |
| 2014/0154722 A1 | 6/2014 | Yeal et al. | |
| 2014/0170671 A1* | 6/2014 | McGarr | C12M 25/04 435/7.1 |
| 2014/0227145 A1 | 8/2014 | Kim et al. | |
| 2014/0273053 A1 | 9/2014 | Lee et al. | |
| 2014/0287960 A1 | 9/2014 | Shepard et al. | |
| 2015/0005180 A9 | 1/2015 | Ishihara et al. | |
| 2015/0086445 A1 | 3/2015 | Lee et al. | |
| 2015/0101070 A1 | 4/2015 | Nam et al. | |
| 2015/0282885 A1 | 10/2015 | King et al. | |
| 2016/0074558 A1 | 3/2016 | Murphy et al. | |
| 2016/0122723 A1 | 5/2016 | Retting et al. | |
| 2016/0348049 A1 | 12/2016 | Baba | |
| 2017/0198275 A1 | 7/2017 | Lee | |
| 2017/0267960 A1* | 9/2017 | Tsukada | C12M 23/20 |

FOREIGN PATENT DOCUMENTS

| | | |
|---|---|---|
| CN | 102246037 A | 11/2011 |
| CN | 102836751 A | 12/2012 |
| CN | 103930066 | 7/2014 |
| CN | 104717987 | 6/2015 |
| CN | 105381903 A | 3/2016 |
| CN | 105521841 | 4/2016 |
| CN | 105964313 A | 9/2016 |
| EP | 1310794 | 5/2003 |
| EP | 3040723 | 7/2016 |
| KR | 20140072883 | 6/2014 |
| KR | 201600336619 | 4/2016 |
| WO | 9309872 A1 | 5/1993 |
| WO | 2001007891 | 2/2001 |
| WO | 2005098432 A1 | 10/2005 |
| WO | 2006078814 A2 | 7/2006 |
| WO | 2007053561 | 5/2007 |
| WO | 2012034022 | 3/2012 |
| WO | 2012125906 | 9/2012 |
| WO | 2012158875 | 11/2012 |
| WO | 2013041901 | 3/2013 |
| WO | 2015121302 A1 | 8/2015 |
| WO | WO-2015178413 A1 * | 11/2015 ............ C12M 23/20 |
| WO | 2017123722 | 7/2017 |

OTHER PUBLICATIONS

English Translation of Office Action from Chinese Application No. 201780071459.2 dated Dec. 3, 2020.
Bull, C. et al., "Sialic acid mimetrics to target the sialic acid-Siglec axis," Trends Biochem Sci. 41(6) 519-531 (2016).
Crocker, P.R. et al., "Siglecs and their roles in the immune system," Nat. Rev. Immunol. 7(4) 255-66 (2007).
Duque, G.A. et al., "Macrophage cytokines: involvement in immunity and infectious diseases," Front Immunol. 5, 491 (2014).
Dwyer, A.R. et al., "A three-dimensional co-culture system to investigate macrophage-dependent tumor cell invasion," J. Biol. Methods 3(3) e49 (2016).
Hangai, S. et al., "Innate immune receptors in the regulation of tumor immunity," In: Zitvogel L., Kroemer G. (eds) Oncoimmunology. Springer. Cham 407-427 (2018).
Iwamoto, M. et al., "Structure-activity relationship of alginate oligosaccarides in the induction of cytokine production from RAS264.7 cells," FEBS. Lett. 579 4423-4429 (2005).
Iwamoto, Y. et al., "Enzymatically depolymerized alginate oligomers that cause cytotoxic cytokine production in human mononuclear cells," Biosci. Biotechnol. Biochem. 67 258-263 (2003).
Joshi, P. et al., "High-content imaging assays on a miniaturized 3D cell culture platform," Tox. In Vitro, 50, 147-159 (2018).
Extended European Search Report for EP Appln. No. 17871475.4 dated Sep. 2, 2020.
Kawasaki T. et al., "Isolation and characterization of a receptor lectin specific for galactose/N-acetylgalactosamine from macrophages," Carbohydr. Res. 151, 197-206 (1986).
Yu, K.N. et al., "High-throughput metabolism-induced toxicity assays demonstrated on a 384-pillar plate," Archives of Toxicology 92 2501-2516 (2018).
Lee, M.Y. et al., "Three-dimensional cellular microarray for microscale toxicology assay," Proceedings of the Natl. Acad. of Sci. of the USA (PNAS), 105(1) 59-63 (2008).
Lepenies, B. et al., "Targeting C-type lectin receptors with multivalent carbohydrate ligands," Adv. Drug Deliv. Rev. 65(9) 1271-1281 (2013).
Lin, K. et al., "Carbohydrate-based polymers for immune modulation," ACS Macro Letters 3(7) 652-657 (2014).
Liu, G. et al., "Modulation of macrophage activation and programming in immunity," J Cell Physiol. 228(3) 502-812 (2013).
Lundahl, M.L.E. et al., "Therapeutic potential of carbohydrates as regulators of macrophage activation," Biochem. Pharmacol. 146, 23-41 (2017).
Mannem, M. et al., "Polyvalent iteractions in biological systems: implications for design and use of multivalent ligands and inhibitors," Angew. Chem. 37(20) 2754-2794 (1998).
May, A.P. et al., "Crystal structure of the N-terminal domain of dialoadhesin in complex with 3' sialyllactose at 1.85 A resolution," Mol. Cell 1(5), 719-728 (1998).
Miyazaki, K. et al., "Colonic epithelial cells express specific ligands for mucosal macrophage immunosuppressive receptors Siglec-7 and -9," J. Immunol. 188(9) 4690-4700 (2012).
Mills, C.D. et al., "Macrophages at the fork in the road to health or disease," Front. Immunol. 6-59 (2015).
Misharin, A.V. et al., "Flow cytometric analysis of macrophages and dendritic cell subsets in the mouse lung," Am. J. Respir. Cell Mol. Biol. 49(4) 503-510 (2013).
Murray, M.Y. et al., "Macrophage migration and invasion is regulated by MMP10 expression," PLoS One. 8(5) e63555 (2013).
O'Neill, A.S. et al., "Sialoadhesin—macrophage-restricted marker of immunoregulation and inflammation," Immunology 138(3) 198-207(2013).

(56) References Cited

OTHER PUBLICATIONS

O'Reilly, M.K. et al., "Siglecs as targets for therapy in immune-cell-mediated disease," Trends Pharmacol. Sci. 30(5) 240-248 (2009).
O'Reilly, M.K., "Multivalent ligands for Siglecs," Methods Enzymol. 478 343-363 (2010).
Roth, A.D. et al., "Polymer coating on a micropillar chip for robust attachment of PuraMatrix peptide hydrogel for 3D hepatic cell culture," Mat. Sci. and Eng C, 90, 634-644 (2018).
Saxena, R.K. et al., "Evidence for lipopolysaccharide induced differentiation of Raw264.7 murine macrophage cell line into dendritic like cells," J. Biosci. (Bangalore) 28(1) 129-134 (2003).
Sharman, J. et al., "An open-label phase 2 trial of entospletinib (GS-9973), a selective spleen tyrosine kinase inhibitor, in chronic lymphocytic leukemia," Blood 125, 2336-2343 (2015).
Sica, A. Mantovani, "Macrophage plasticity and polarization: in vivo veritas," J. Clin. Invest. 122(3), 787-795 (2012).
Spence, S. et al., "Targeting Siglecs with a sialic acid-decorated nanoparticle abrogates inflammation," Sci. Transl. Med., 7 303ra140 (2015).
Stenken, J.A. et al., "Bioanalytical chemistry of cytokines—a review," Analytica Chimica Acta 853 95-115 (2015).
Tang, J. et al., Straightforward Synthesis of N-Glycan Polymers from Free Glycans via Cyanoxyl Free Radical-Mediated Polymerization, ACS MacroLetters 6, 107-111 (2017).
Wang, D. et al., "Globally profiling sialylation status of macrophages upon statin treatment," Glycobiology, 25, 1007-1015 (2015).
Wu, G.J. et al., "Chitooligosaccharides from the shrimp chitosan hydrolysate induces differentiation of murine RAW264.7 macrophages into dendritic-like cells," J. Funct. Foods 12 70-79 (2015).
International Search Report and Written Opinion from PCT/US17/013144 dated Mar. 30, 2017.
Lee, D.W. et al., "Automatic 3D Cell Analysis in High-Throughput Microarray Using Micropillar and Microwell Chips," Journal of Biomolecular Screening, 2015, 1178-1184, Society for Laboratory Automation and Screening.
Kwon, S.J. et al., "High-throughput and combinatorial gene expression on a chip for metabolism-induced toxicology screening," Nature Communications, May 6, 2014, 5:3739, DOI 10.1038/ncomms4739, 2014 Macmillan Publ. Ltd.
Lee, D.W. et al., "High-Throughput Screening (HTS) of Anticancer Drug Efficacy on a Micropillar/Microwell Chip Platform," Analytical Chemistry, 2014, 86(1), 535-542, ACS Publications.
Lee, D.W. et al., "Application of the DataChip/MetaChip technology for the evaluation of ajoene toxicity in vitro," Archives of Toxicology, 88(2), 283-290, Jul. 28, 2013 Springer.
Lee, D.W. et al., "Plastic pillar inserts for three-dimensional (3D) cell cultures in 96-well plates," Sensors and Actuators B, 177(1), 2013, 78-85, Elsevier B.V.
Zhang, H.Y. et al., "High-Throughput Transfection of Interfering RNA into a 3D Cell-Culture Chip," Small, 8(13), 2091-2098, Jul. 2012.
Fernandez, T.G. et al., "Three-Dimensional Cell Culture Microarray for High-Throughput Studies of Stem Cell Fate," Biotechnology and Bioengineering, vol. 106, No. 1, 106-118, May 1, 2010.
Park, T.J., et al., "Signal Amplification of Target Protein on Heparin Glycan Microarray," Analytical Biochemistry, 383, 116-121, Dec. 1, 2008.
Fernandes, T.G. et al., "On-Chip, Cell-Based Microarray Immunofluorescence Assay for High-Throughput Analysis of Target Proteins," Analytical Chemistry, 80, 6633-6639, Sep. 1, 2008.
Lee, M.Y. et al., "Three-dimensional cellular microarray for high-throughput toxicology assays," Proc. of the Nat'l. Academy of Sciences (PNAS), 105(1), 59-63, Jan. 8, 2008.
Kwon, S.J. et al., "High-Throughput, Microarray-Based Synthesis of Natural Product Analogues via in vitro Metabolic Pathway Construction," ACS Chemical Biology, 2(6), 419-425, May 25, 2007.
Lee, M.Y. et al., "Human P450 Microarrays for In Vitro Toxicity Analysis: Toward Complete Automation of Human Toxicology Screening," Journal of the Assn. for Lab. Automation, 11(6), 374-380, Dec. 2006.
Lee, M.Y. et al., "Metabolizing enzyme toxicology assay chip (MetaChip) for high-throughput microscale toxicity analyses," Proc. of the Nat'l. Academy of Sciences (PNAS), 102(4), 983-987, Jan. 25, 2005.
Lee, D.W. et al., "High-Throughput, Miniaturized Clonogenic Analysis of a Limiting Dilution Assay on a Micropillar/Microwell Chip with Brain Tumor Cells," Small, 10(24), 5098-5105, 2014 Wiley-VCH Verlag GmbH & Go. KGaA, Weinheim.
International Search Report and Written Opinion from PCT/US17/062266 dated Mar. 7, 2018.
Lee, D.W. et al., "Estimation of bisphenol A—Human toxicity by 3D cell culture arrays, high throughput alternatives to animal tests," Toxicology Letters, 259, 87-94 (2016).
Kang, J.H. et al., "Mini-pillar array for hydrogel-supported 3D culture and high-content histologic analysis of human tumor spheroids," Lab on a Chip, DOI: 10. 1039/c6lc00526h (2016).
Datar, et a. "Biocompatible hydrogels for microarray cell priting and encapsulation." Biosensors 2015, vol. 5, pp. 647-663 (published Oct. 26, 2015).

* cited by examiner

CHIP PLATFORMS FOR MICROARRAY 3D BIOPRINTING

CROSS REFERENCE TO RELATED APPLICATIONS

This application claims the benefit of Provisional Application No. 62/423,586 filed on Nov. 17, 2016, and is hereby incorporated by reference in its entirety into this application.

BACKGROUND

When developing therapeutic drugs, it is important to determine a drug's safety and efficacy. In the relatively early stages of drug development, drug safety and efficacy is often tested outside the living organism ("in vitro"). The in vitro assays currently available, however—using 2D cell monolayers or 3D cell spheroids—do not adequately mimic how drugs act in the living organism ("in vivo"). Thus, an in vitro cell/tissue model that can closely mimic the corresponding tissues in vivo and systematically simulate diseases is desired.

3D bioprinting is a promising technology in this regard. Generally, 3D bioprinting refers to robotically dispensing cells layer-by-layer in hydrogels, thus creating relatively large scale tissue constructs that more accurately mimic the in vivo environment. But because the tissue constructs are generally on a large scale, 3D bioprinting is not ideal for high throughput testing, and is thus limited as an alternative to the currently available in vitro assays. Recently, however, a method of microarray 3D bioprinting was developed, which allows for high throughput testing.

Microarray 3D bioprinting refers to dispensing very small amounts of cells along with other biological samples such as hydrogels, growth factors, extracellular matrices, biomolecules, drugs, DNAs, RNAs, viruses, bacteria, growth media, or combinations thereof, on a microwell/micropillar chip platform using a microarray spotter and then incubating the cells to create a mini-bioconstruct. This technology can potentially revolutionize tissue engineering and disease modeling for screening therapeutic drugs and studying toxicology.

Since microwell/micropillar chip platforms (also known as "microarray biochips") contain arrays of up to 5,000 microwells/micropillars, this method is ideal for high throughput testing. However, the currently available microwell/micropillar chips are not ideal for microarray 3D bioprinting due to the limited space available on the micropillar chip or limited control of individual experimental conditions in the microwell chip.

For example, currently available micropillar chips use pillars with flat tops, which are not conducive to dispensing cells layer-by-layer. Thus, it is difficult to carry out 3D bioprinting on micropillar chips. In addition, the currently available microwell chips use wells that trap air bubbles in the hydrogel as the cell layers are printed. In addition, it is difficult to control each bioprinted tissue construct individually in the microwell chip because all tissue constructs in the microwell chip should be immersed in a petri dish with a universal growth medium. Thus, there is a need for designing a new structure of microwells and micropillars on a chip that can facilitate layered cell printing on both the pillar and well, ensure robust cell spot attachment for high-content imaging and immunofluorescent assays, and avoid air bubble entrapment for robust 3D cell/tissue cultures. The new chip design can be compatible with conventional microtiter plates, including 96-, 384-, and 1536-well plates.

SUMMARY

The present invention is directed to a micropillar chip and a microwell chip that facilitates layered cell printing on both the pillar and well, ensures robust cell spot attachment for high-content imaging and immunofluorescent assays, and avoids air bubble entrapment. The present invention is further directed to methods using the micropillar and microwell chips to create miniature multicellular biological constructs.

The micropillar chip comprises a chip base with at least one micropillar. The micropillar, rather than having a flat top, has a pillar-microwell at its top end. The pillar-microwell comprises a pillar-microwell base and a side wall extending upwardly from the base.

The microwell chip comprises at least one microwell that, unlike conventional microwells, has an upper and lower microwell.

The method of creating a miniature multicellular biological construct comprises depositing cells into a pillar-microwell, exposing the pillar-microwell to growth media, and incubating the cells.

These and other features, aspects, and advantages of the general inventive concepts will become better understood with reference to the following description and appended claims.

18C illustrates the surface chemistry of an embodiment of a method of attaching antibodies to micropillars.

Figure 19:
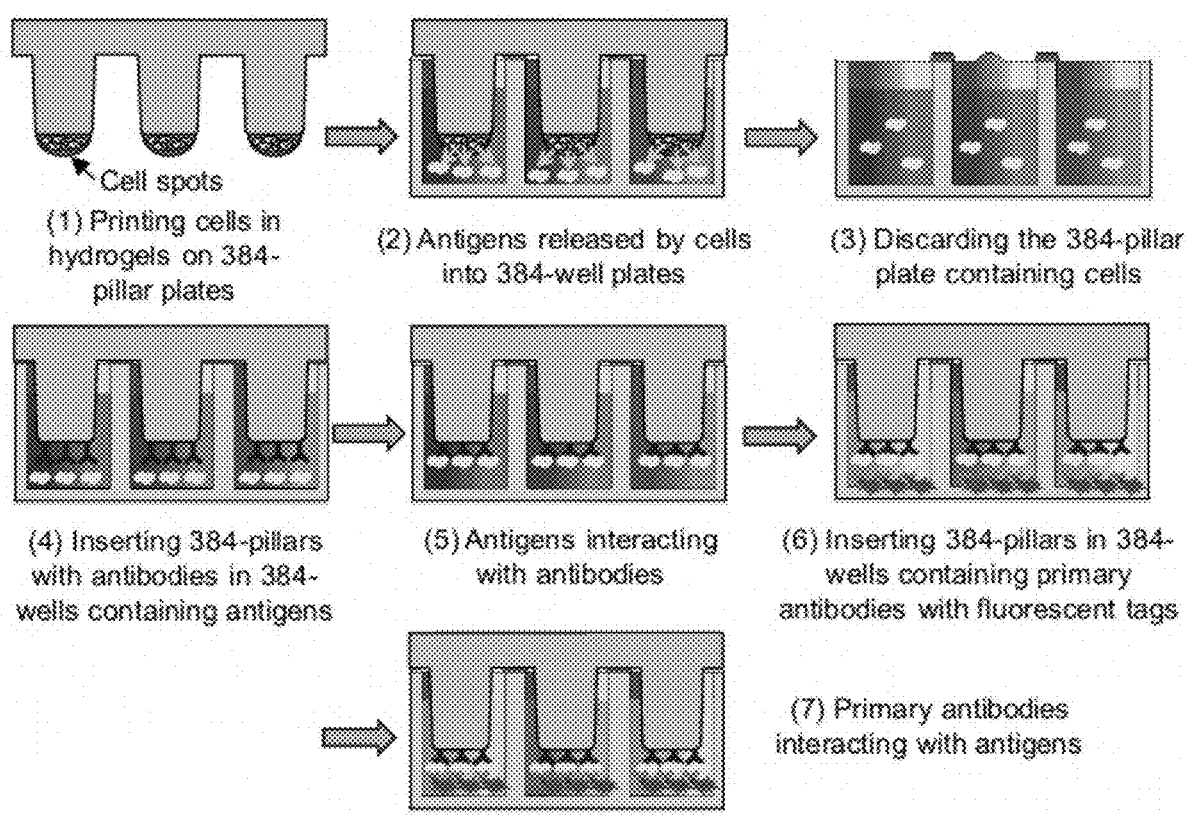

FIG. 19 shows a flowchart demonstrating an embodiment of a method of detecting biomarkers.

Figure 20:
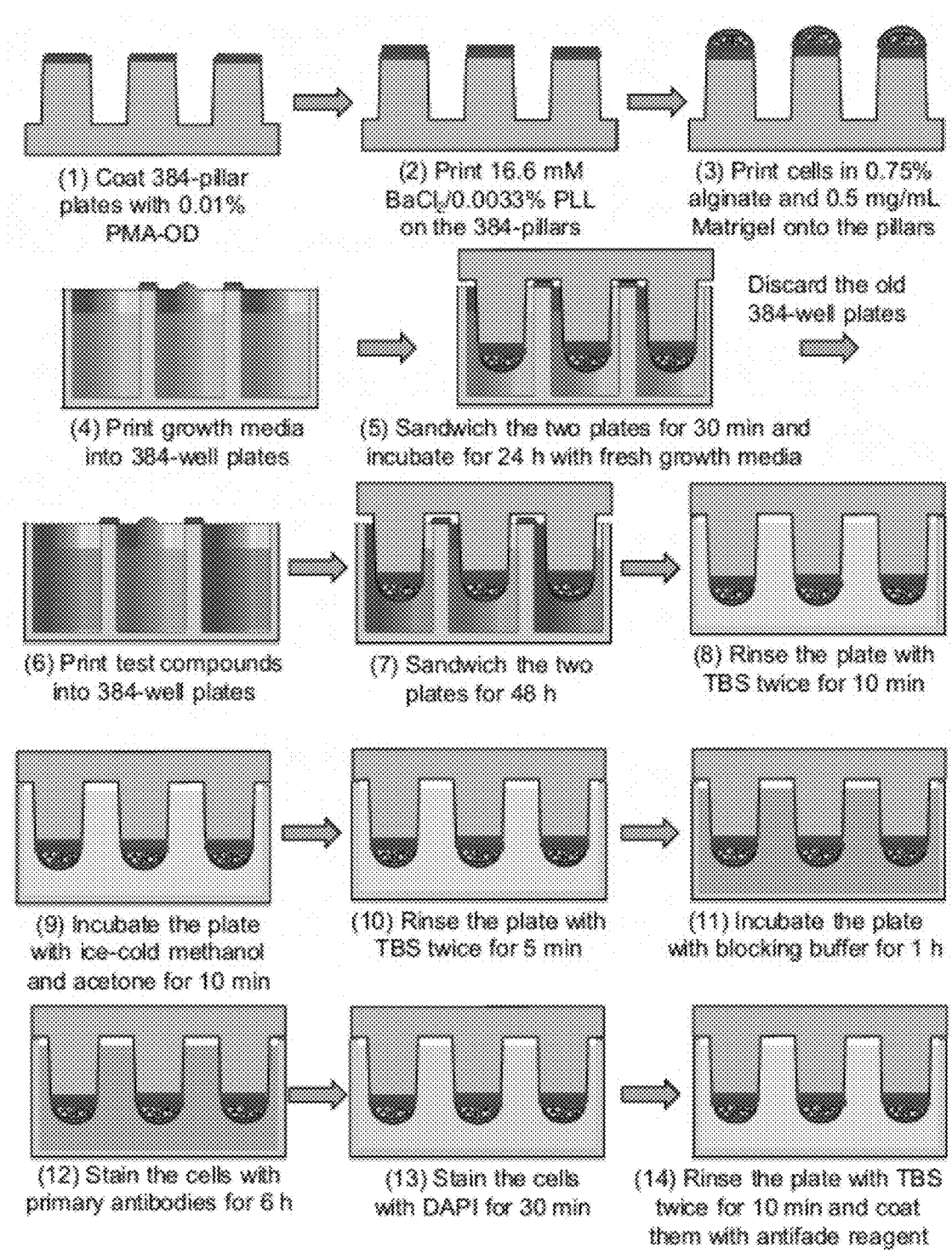

FIG. 20 shows a flowchart demonstrating an embodiment of a method of measuring changes in cell surface markers.

Figure 21:
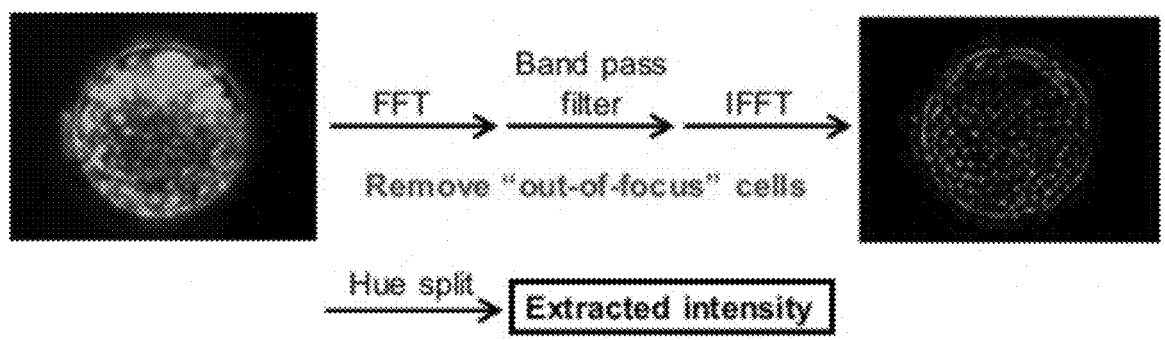

FIG. 21 shows a flowchart demonstrating an embodiment of a method of quantifying cancer cell migration and images of stained Hep3B cells.

Figure 22A:
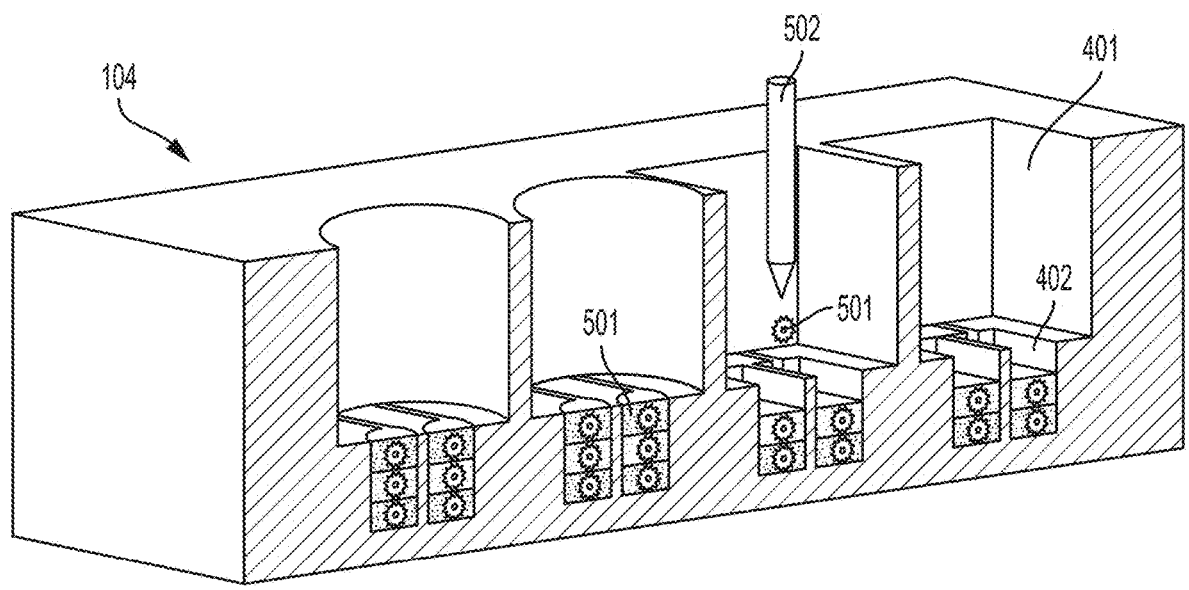

FIG. 22A shows a sectional view of an embodiment of a microwell chip.

Figure 22B:
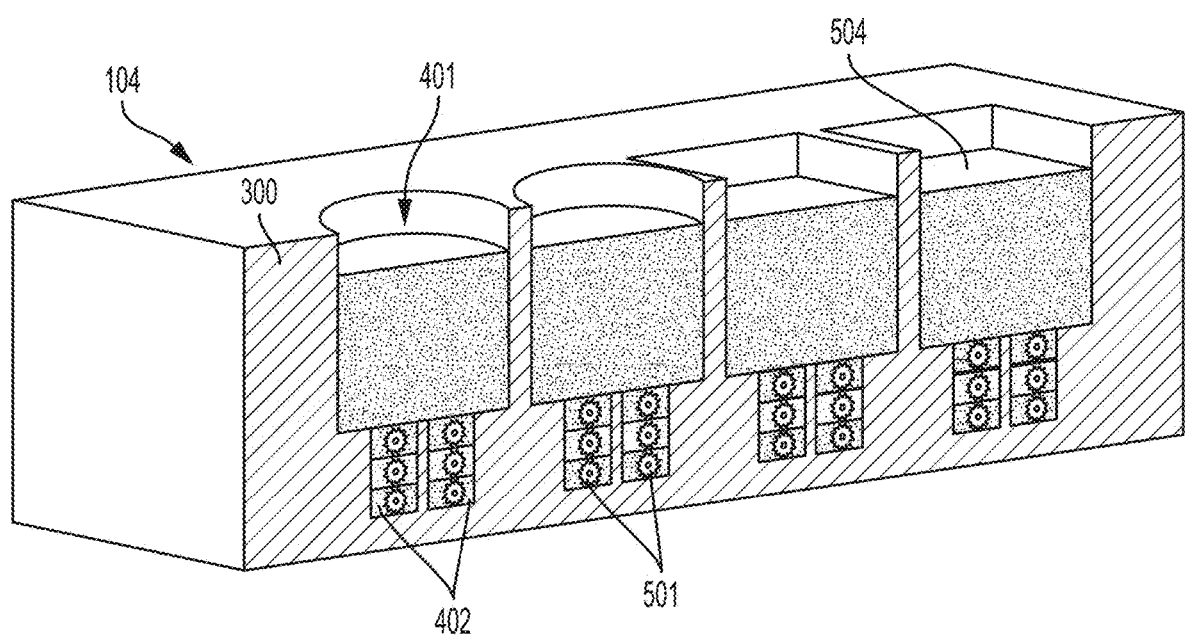

FIG. 22B shows a sectional view of an embodiment of a microwell chip.

Figure 23:
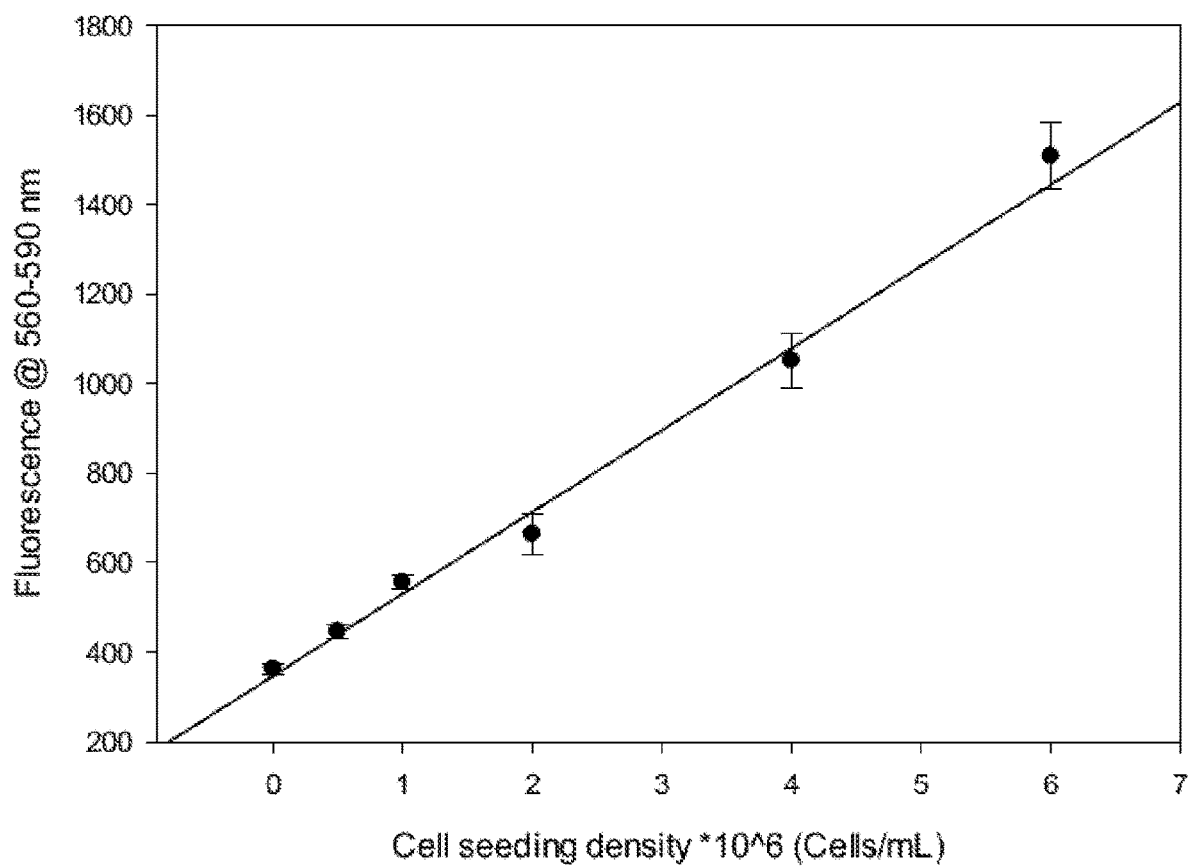

FIG. 23 shows a line graph that plots the data from Example 3.

DETAILED DESCRIPTION

While various exemplary embodiments and methods are described herein, other embodiments, methods, and materials similar or equivalent to those described herein are encompassed by the general inventive concepts. All references cited herein, including published or corresponding U.S. or foreign patent applications, issued U.S. or foreign patents, and any other references, are each incorporated herein by reference in their entireties, including all data, tables, figures, and text presented in the cited references.

Unless defined otherwise, all technical and scientific terms used herein have the same meaning as commonly understood by one of ordinary skill in the art to which the invention belongs.

All percentages, parts, and ratios as used herein are by weight of the total formulation, unless otherwise specified. All such weights as they pertain to listed ingredients are based on the active level and, therefore, do not include solvents or by-products that may be included in commercially available materials, unless otherwise specified.

All references to singular characteristics or limitations of the present disclosure shall include the corresponding plural characteristic or limitation, and vice versa, unless otherwise specified or clearly implied to the contrary by the context in which the reference is made.

The methods and embodiments of the present disclosure can comprise, consist of, or consist essentially of the essential elements of the disclosure as described herein, as well as any additional or optional element described herein or which is otherwise useful in carrying out the general inventive concepts.

To the extent that the terms "includes," "including," "contains," or "containing" are used in the specification or the claims, they are intended to be inclusive in a manner similar to the term "comprising" as that term is interpreted when employed as a transitional word in a claim. Furthermore, to the extent that the term "or" is employed (e.g., A or B) it is intended to mean "A or B or both." When the applicants intend to indicate "only A or B but not both" then the term "only A or B but not both" will be employed. Thus, use of the term "or" herein is the inclusive, and not the exclusive use. Also, to the extent that the terms "in" or "into" are used in the specification or the claims, it is intended to additionally mean "on" or "onto."

All combinations of method or process steps as used herein can be performed in any order, unless otherwise specified or clearly implied to the contrary by the context in which the referenced combination is made.

All ranges and parameters, including but not limited to percentages, parts, and ratios, disclosed herein are understood to encompass any and all sub-ranges assumed and subsumed therein, and every number between the endpoints. For example, a stated range of "1 to 10" should be considered to include any and all sub-ranges beginning with a minimum value of 1 or more and ending with a maximum value of 10 or less (e.g., 1 to 6.1, or 2.3 to 9.4), and to each integer (1, 2, 3, 4, 5, 6, 7, 8, 9, and 10) contained within the range.

The general inventive concepts are directed to micropillar and microwell chips for microarray analysis that facilitate layered cell printing on both the micropillar and in the microwell. The micropillar and microwell chips ensure robust cell spot attachment for high-content imaging and immunofluorescent assays, and avoid air bubble entrapment. The general inventive concepts also contemplate methods of creating and analyzing miniature multicellular biological constructs ("mini-bioconstructs") using the inventive micropillar and microwell chips.

Conventional microarray biochips are designed so that the micropillar chip mates with the microwell chip. The micropillars are sized so that they may be inserted into the corresponding microwells. The micropillar and microwell chips of this invention may be compatible with each other and with conventional micropillar and microwell chips or microtiter plates. For example, the inventive micropillar chip may be compatible with a conventional microwell chip and conventional microtiter plates and the inventive microwell plates, and the inventive microwell chip may be compatible with a conventional micropillar chip and the inventive micropillar chip. An exemplary conventional micropillar/microwell chip is made by Samsung Electro Mechanics, Co. and MBD Korea (e.g., S+ Microwell Chip). Exemplary conventional microtiter plates, including 96-, 384-, 1536-, and 3456-well plates are made by Corning and other manufacturers.

The inventive chips may be made of a biocompatible polymer. The biocompatible polymer may be clear or opaque depending on the type of analysis to be performed. For example, in some exemplary embodiments, the chip may be made of clear polystyrene. In some further exemplary embodiments, the chip may be made of functional poly(styrene-co-maleic anhydride). The chip may be manufactured using any conventional manufacturing process, including 3D printing.

Figure 1A:
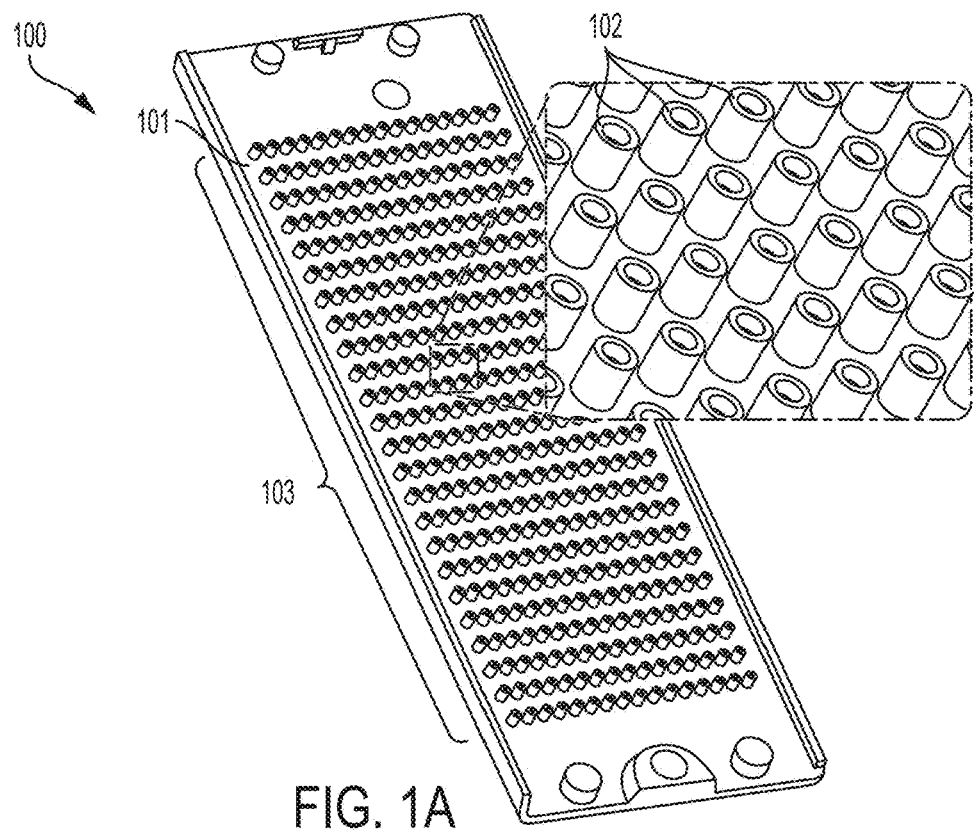
FIG. 1A shows an embodiment of a micropillar chip.
Figure 1B:
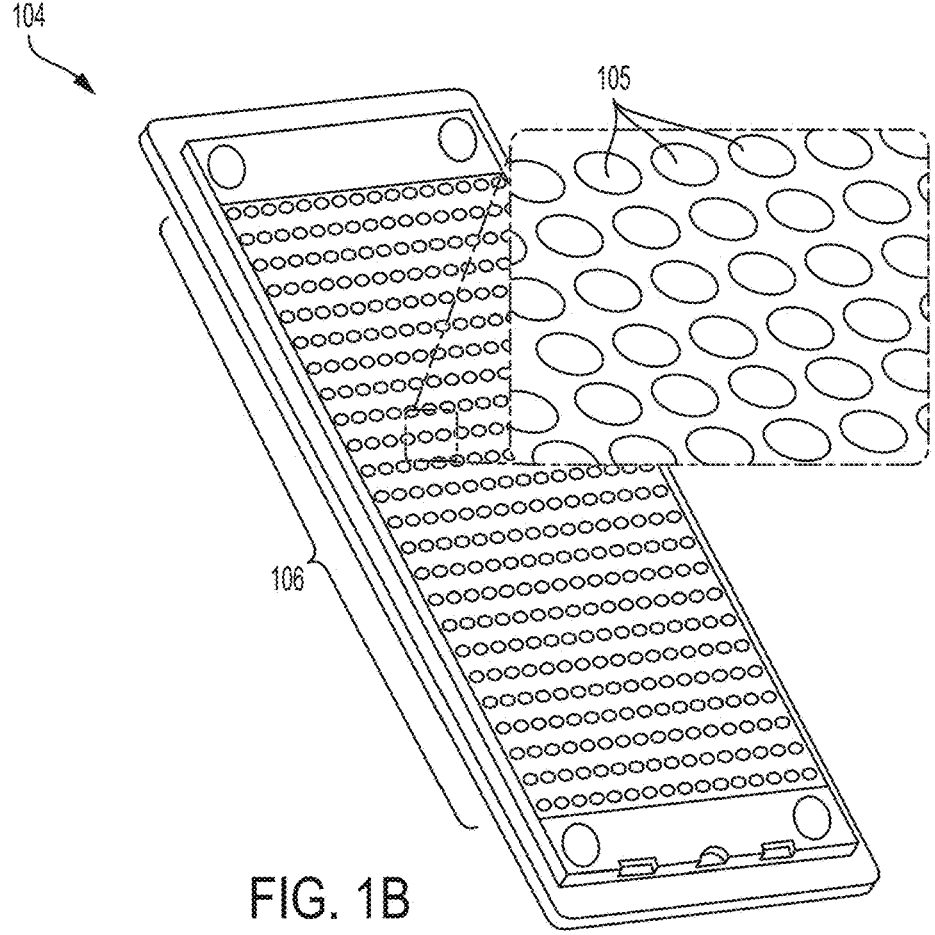
FIG. 1B shows an embodiment of a microwell chip.

Referring to FIG. 1, the inventive micropillar chip 100 comprises a chip base 101 and at least one micropillar 102. In some exemplary embodiments, the micropillar chip contains arrays of micropillars 103, for example, about 90 to about 5,000 micropillars. The micropillar 102 may be any shape depending on the needs of the test. For example, the micropillar may be cylindrical 201 or it may be square 202. An embodiment of a plate containing an array of 384 pillars is depicted in FIG. 1.

In some exemplary embodiments, the micropillar 102 is from about 0.3-5 mm in width, about 0.3-5 mm in length, and about 1-20 mm in height. In some further exemplary embodiments, the micropillar 102 may be from about 0.3-5 mm in diameter and 1-20 mm in height. For example, a micropillar 102 may be 2.6 mm in diameter and 13.5 mm in height.

Figure 2A:
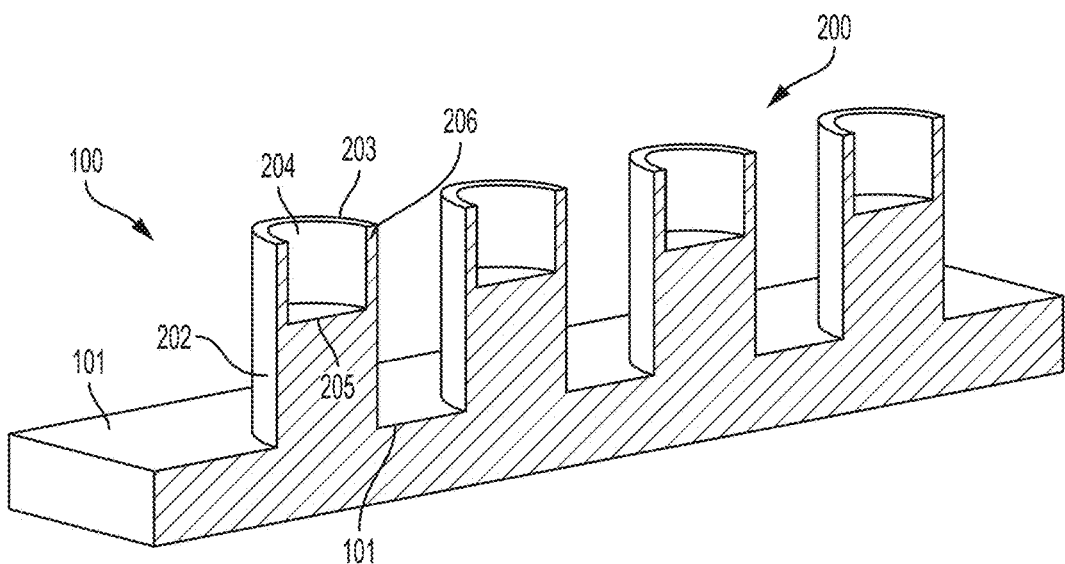
FIG. 2A shows a sectional view of embodiments of micropillars.
Figure 2B:
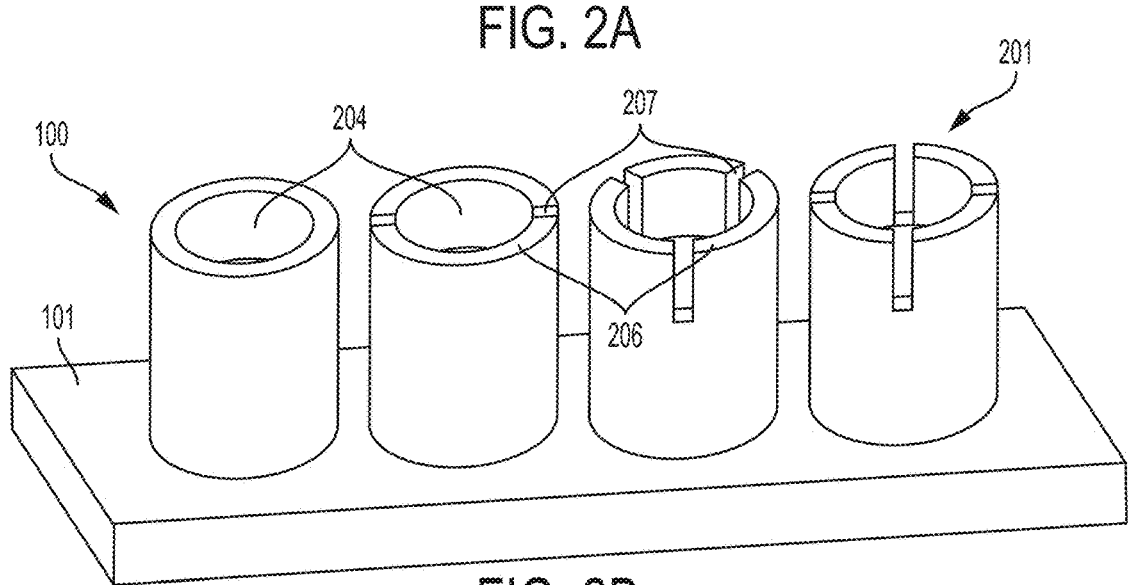
FIG. 2B shows a perspective view of embodiments of micropillars.
Figure 2C:
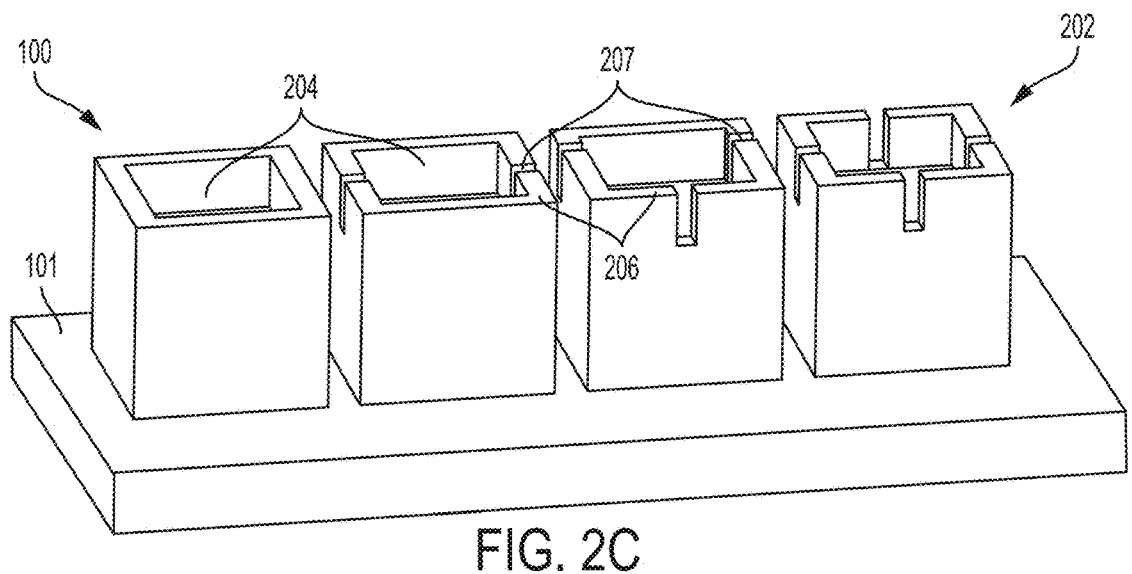
FIG. 2C shows a perspective view of embodiments of micropillars.

Referring to FIG. 2, unlike conventional micropillars that have flat tops, the inventive micropillar 102 comprises a top end 203 that contains a pillar-microwell 204. The pillar-microwell 204 is a reservoir with a pillar-microwell base 205 and at least one sidewall 206. The pillar-microwell may extend from the top end 203 of the micropillar to the pillar-microwell base 205. The pillar-microwell base may be anywhere between the chip base 101 and pillar top end 203. For example, the pillar-microwell may be capable of holding any volume of sample, including 1-4 μL. The sidewall may be anywhere from about 0.5-5 mm in height and about 0.3-1 mm in thickness. The pillar-microwell sidewall 206 facilitates layer-by-layer cellular printing and robust cell spot attachment.

In some exemplary embodiments, the micropillar chip contains a means for minimizing air bubble entrapment. For example, in some exemplary embodiments, the pillar-microwell sidewall 206 may contain at least one slit 207. The slit 207 is a gap in the sidewall that extends at least partway through the width of the sidewall. In some further exemplary embodiments, the pillar-microwell sidewall may contain 1-5 slits 207, or more.

Figure 3:
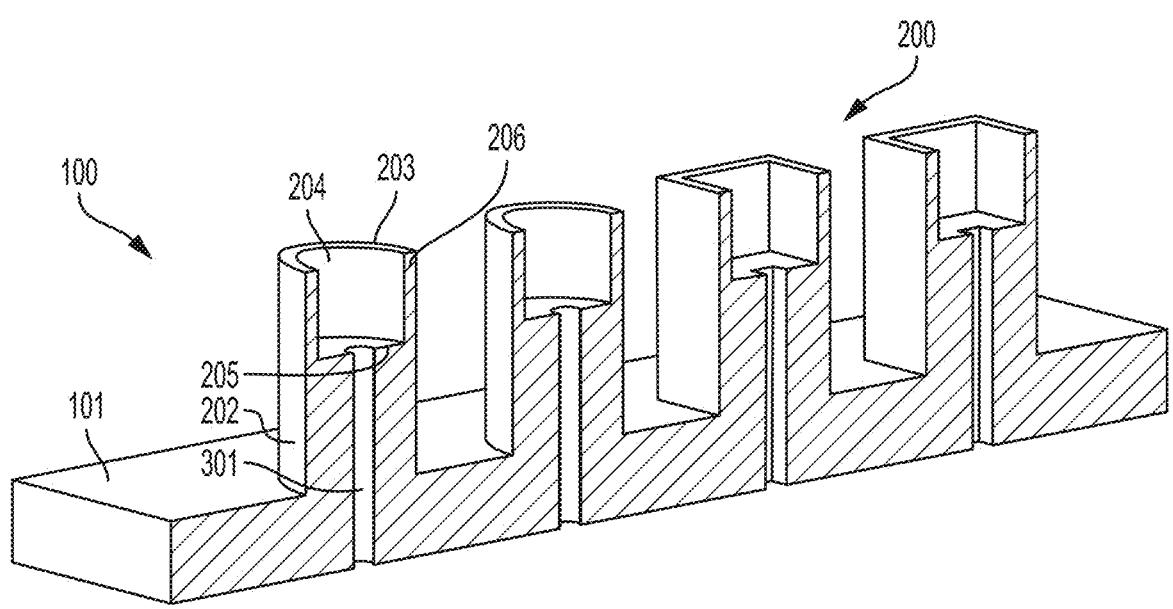
FIG. 3 is a sectional view of embodiments of micropillars.

Referring to FIG. 3, in another exemplary embodiment in which the micropillar chip contains a means for minimizing air bubble entrapment, the micropillar 102 contains a bore 301 that extends from the pillar-microwell base 205 at least partially through the micropillar. In some exemplary embodiments, the diameter of the bore may be less than the diameter of the micropillar. For example, in some exemplary embodiments, the diameter of the bore may be, but is not limited to, 0.4 mm for a pillar with a diameter of 2 mm, or the diameter of the bore may be, but is not limited to, 1 mm for a pillar with a diameter of 5 mm.

Further, in some exemplary embodiments, the pillar-microwell base 205 may be plasma treated or coated with functional polymers to enhance robust cell spot attachment. Exemplary functional polymers include, but are not limited to, poly(maleic anhydride-alt-1-octadecene) (PMA-OD), poly(maleic anhydride-alt-1-tetradecene) (PMA-TD), polyethylene oxide-maleic anhydride copolymers, including ACM1510, ADM1510, AEM1510, AKM0530, and AKM1510, poly-L-lysine (PLL), barium chloride ($BaCl_2$), calcium chloride ($CaCl_2$) collagen, PuraMatrix, fibrinogen, fibronectin, and Matrigel.

Figure 4:
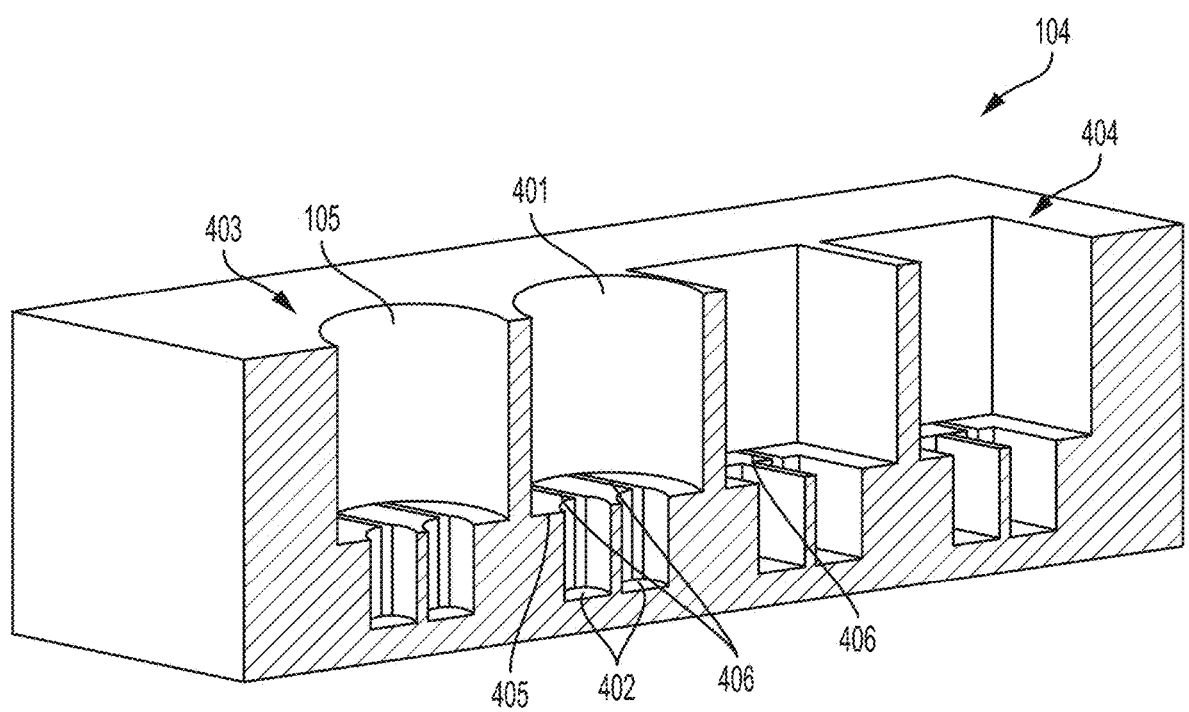
FIG. 4 is a sectional view of embodiments of microwells.
Figure 5A:
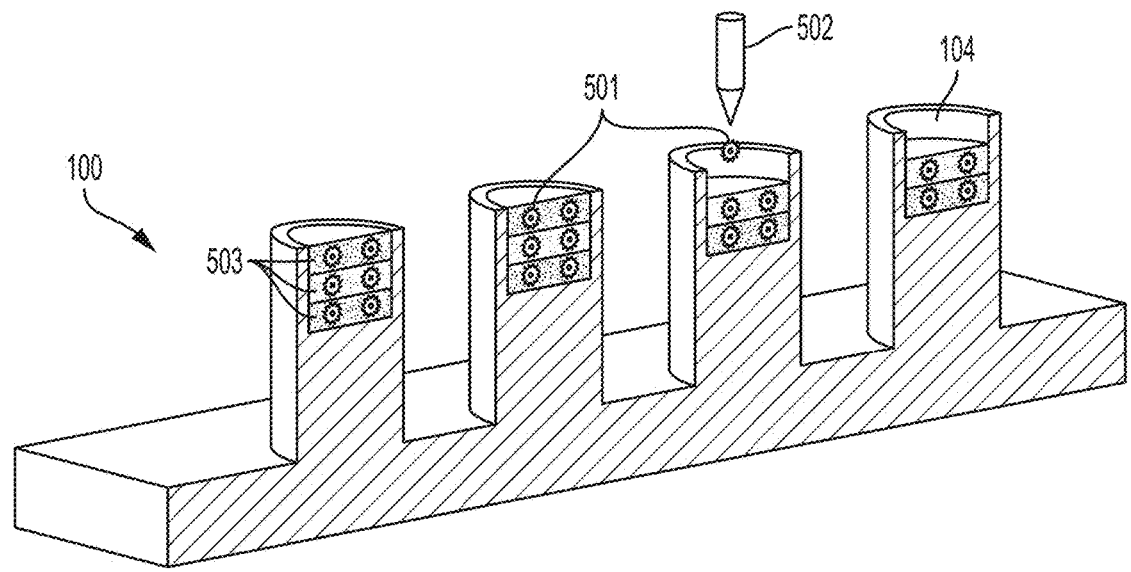
FIG. 5A is a sectional view of embodiments of micropillars with pillar-microwells containing cells.
Figure 5B:
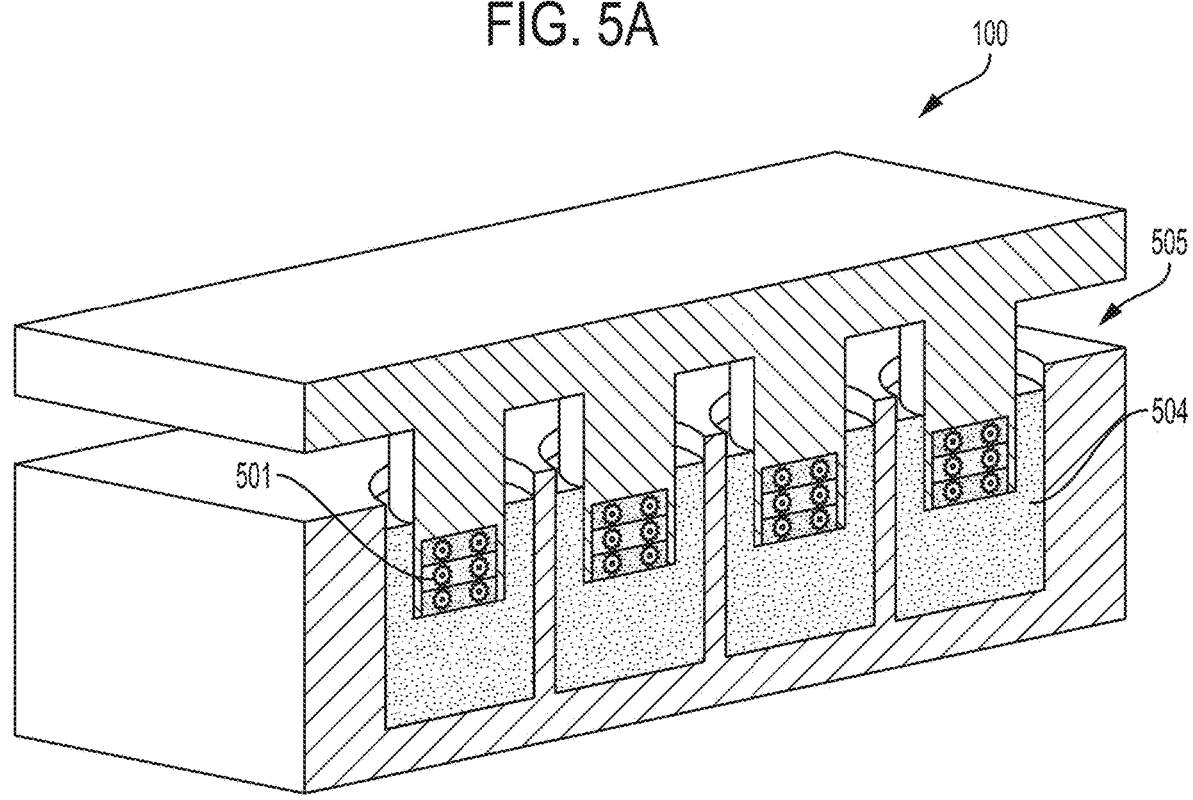
FIG. 5B is a sectional view of embodiments of micropillars with pillar-microwells containing cells sandwiched with a microtiter plate containing growth media.

Referring to FIG. 4, the inventive microwell chip 104 comprises at least one microwell 105. In some exemplary embodiments, the microwell chip may contain an array of microwells 106, for example, about 90 to about 5,000 microwells.

Unlike conventional microwells, the inventive microwell 105 comprises an upper microwell 401 and at least one lower microwell 402. The lower microwell may extend generally downward from the upper microwell base 405. The upper and lower microwells may be in fluid communication.

The upper 401 and lower 402 microwells may be any shape depending on the needs of the test. For example, the microwells may be cylindrical 403 or square 404. In some exemplary embodiments, the upper microwell 401 is from about 0.3-100 mm in width, about 0.3-100 mm in length, and about 0.3-100 mm in height. In some further exemplary embodiments, the upper microwell 401 may be from about 0.3-100 mm in diameter and 0.3-100 mm in height. In some further exemplary embodiments, the upper microwell may be about 1.2 mm in diameter and about 1.5 mm in height. The lower microwell 402 may be smaller than the upper microwell in either width, length, or diameter, depending on the shape.

In some exemplary embodiments, the lower microwell 402 contains a means for minimizing air bubble entrapment. For example, in one exemplary embodiment, at least one peripheral channel 406 extends vertically along the periphery of the lower microwell 402. The dimensions of the peripheral channel 406 may vary in size and shape. For example, the peripheral channel may be rectangular or cylindrical. The peripheral channel may extend from the upper microwell base 405 to the bottom of the lower microwell.

In some further exemplary embodiments, the lower microwell may be plasma treated or coated with functional polymers to enhance robust cell spot attachment.

Referring to FIGS. 5-9, the inventive micropillar and microwell chips enable several inventive methods for microarray 3D bioprinting. One exemplary method generally comprises dispensing cells 501 into at least one pillar-microwell 204 and incubating the cells to create a desired mini-bioconstruct. In some exemplary embodiments, the mini-bioconstructs may be created to mimic particular tissues such as, but not limited to, a heart, liver, or brain. For example, human liver tissue constructs may be created by printing primary hepatocytes/HepaRG, hepatic sinusoidal endothelial cells, hepatic stellate cells, and Kupffer cells layer-by-layer in collagen to maintain liver-specific functions. Also, for example, human brain tissues can be generated by printing neural stem cells in Matrigel and differentiating into different neural lineages for several months.

In some exemplary methods, cells 501 are dispensed into the pillar-microwell 204 by a microarray spotter 502. A microarray spotter 502 is a robotic device capable of dispensing small amounts of liquid, also known as "spots." In some exemplary methods, the microarray spotter 502 may be capable of printing spots into multiple pillar-microwells 204 on the same micropillar chip 100. The microarray spotter may be capable of printing from about 20 nL to about 3000 nL of cells into the pillar-microwells 204. Exemplary microarray spotters include S+ MicroArrayer, commercially available from Samsung, and MBD Korea, as well as MicroSys, PixSys, and CellJet from DigiLab.

In some exemplary methods, prior to dispensing cells, a cell suspension may be made comprising the cells, at least one hydrogel, and growth media. Optionally, one or more biomolecules, drugs, DNAs, RNAs, proteins, bacteria, viruses, or combinations thereof may be included in the cell suspension. For example, the biomolecules, drugs, DNAs, RNAs, proteins, bacteria, viruses, or combinations thereof may be chosen to mimic a particular biological environment, such as particular tissue (liver, heart, brain, etc.).

A hydrogel is generally a polymer that contains water. For example, suitable hydrogels may be alginate, methacrylated alginate, chitosan, hyaluronic acid, fibrinogen, collagen, methacrylated collagen, PuraMatrix, Matrigel, PepGel, and polyethylene glycol. The cells may be entrapped in a hydrogel using various mechanisms such as, but not limited to, ionic, photo, enzymatic, and chemical crosslinking. Crosslinking agents may include salts or enzymes that facilitate gelling of the hydrogel. Examples of suitable crosslinking mechanisms include ionic crosslinking (e.g., alginate with barium chloride and calcium chloride; PuraMatrix with salts), affinity/covalent bonding (e.g., functionalized polymers with streptavidin and biotin), photopolymerization (e.g., methacrylated alginate with photoinitiators), and biocatalysis (e.g., fibringen with thrombin).

The cell suspension concentration may be from about 10,000 to about 20 million cells/mL, about 500,000 to about 5 million cells/mL, or about 1 million to about 2 million cells/mL. The growth media may be from about 90 w/v % to about 99.9 w/v % of the final cell suspension. The hydrogel may be from about 0.1 w/v % to about 10 w/v % of the final cell-suspension.

Growth media is generally a liquid designed to support cell growth. Suitable examples of growth media may include Dulbecco's Modified Eagle Medium (DMEM), Roswell Park Memorial Institute Medium (RPMI), and William's E Medium. Biomolecules may include molecules that support cellular or tissue growth, such as extracellular matrices (ECMs), growth factors, compounds, cytokines, and carbohydrates.

In some further exemplary methods, prior to dispensing the cells with the microarray spotter 502, the pillar-microwells 204 are treated with plasma or coated with functional polymers for cell spot attachment and hydrogel gelation.

Referring to FIGS. 6A-6D, in some exemplary methods, rather than dispense the cells 501 into pillar-microwells 204 with a microarray spotter 502, pillar-microwells may be treated with functional polymers and then submerged in a conventional microtiter plate 505 that contains cells suspended in a hydrogel 602, such as alginate. When the pillar-microwells 204 on the micropillar chip 100 are submerged 603 into the hydrogel 602, the pillar-microwells entrap a portion of the hydrogel 604, so that when the micropillar chip is removed, the pillar-microwells 204 contain a portion of the hydrogel 604. In this method, the volume of cells entrapped in the pillar-microwell may be controlled by the surface area of the pillar-microwell base 205, side walls 206, and slits 207.

Figure 6A:
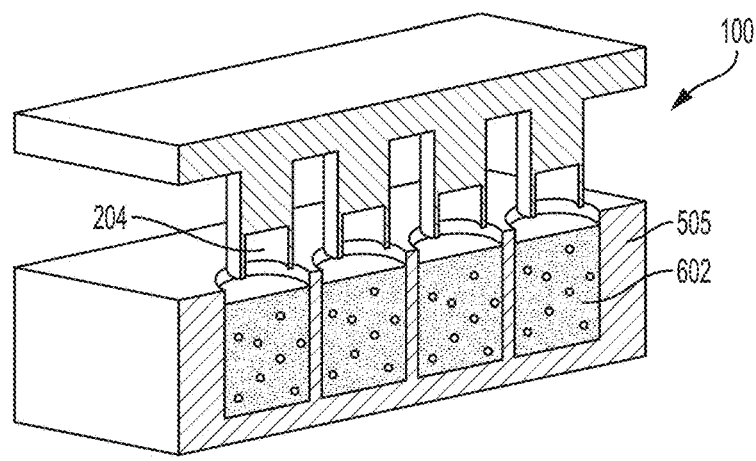
FIG. 6A shows a sectional view of embodiments of micropillars and a microtiter plate.
Figure 6B:
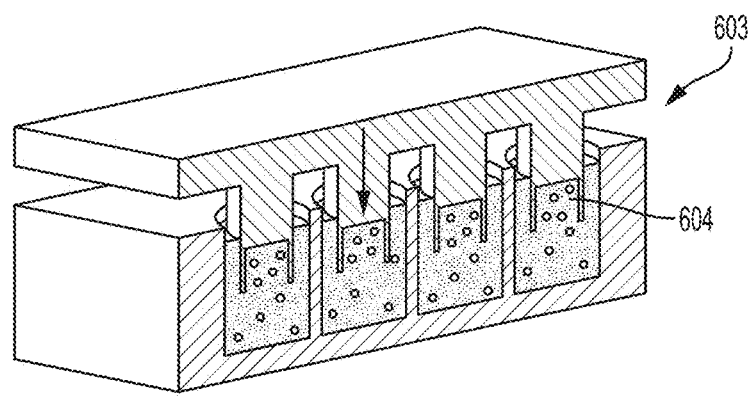
FIG. 6B shows a sectional view of embodiments of micropillars sandwiched with a microtiter plate.
Figure 6C:
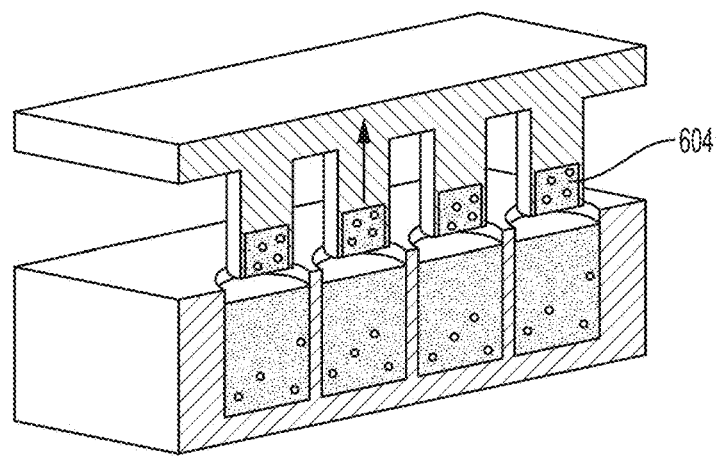
FIG. 6C shows a sectional view of embodiments of micropillars and a microtiter plate.
Figure 6D:
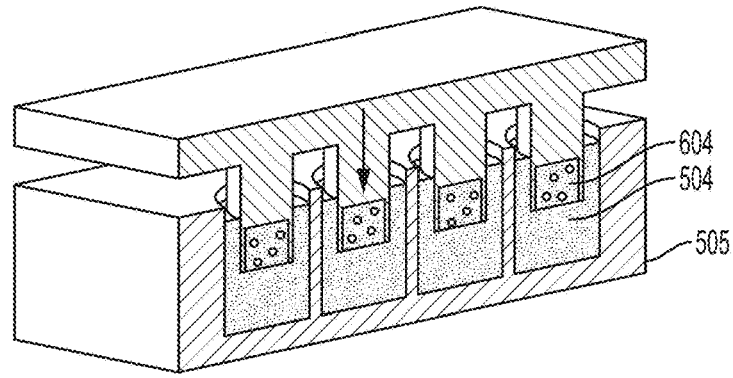
FIG. 6D shows a sectional view of embodiments of micropillars sandwiched with a microtiter plate.
Figure 7A:
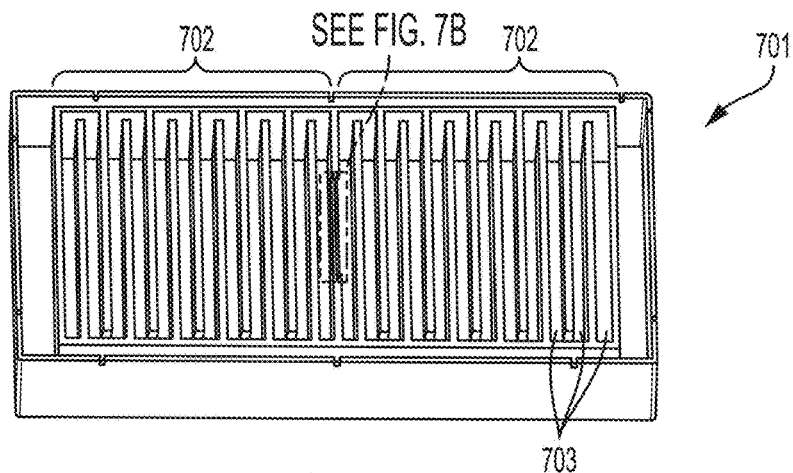
FIG. 7A shows an embodiment of a perfusion channel chip.
Figure 7B:
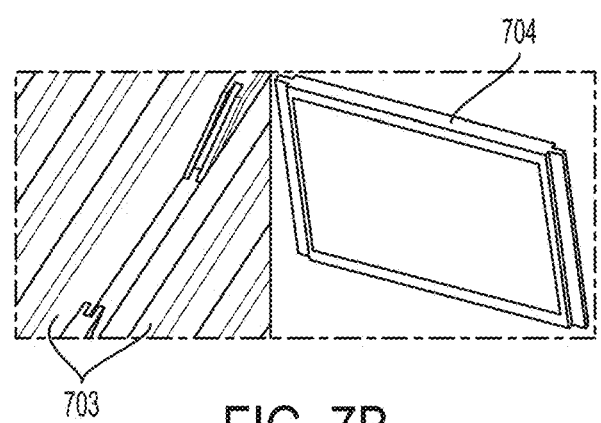
FIG. 7B shows a blown-up section of FIG. 7A.
Figure 7C:
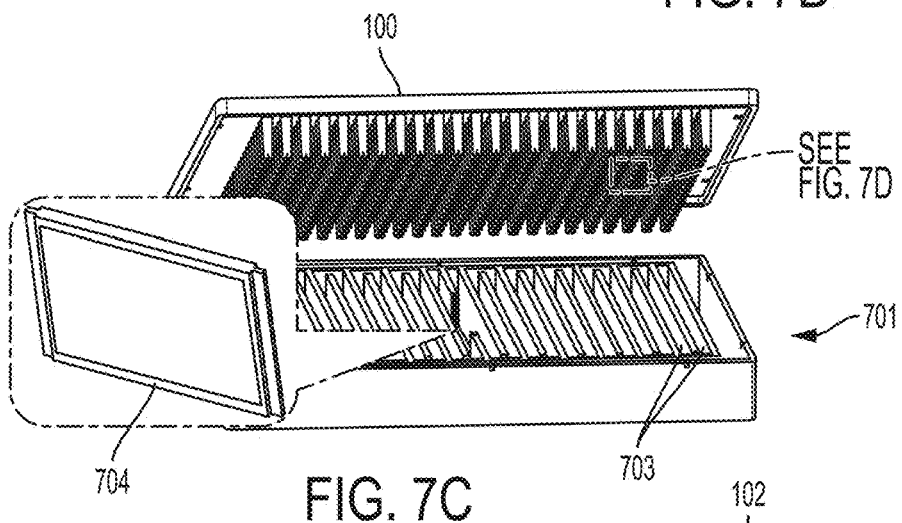
FIG. 7C shows an exploded view of a micropillar paired with a perfusion channel chip.
Figure 7D:
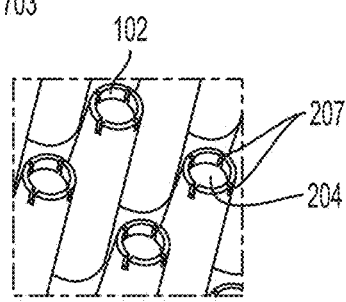
FIG. 7D shows a blown-up section of FIG. 7C.

In some exemplary methods, once the pillar-microwell 204 contains the desired cells, the micropillar plate 100 may be incubated. In some exemplary methods, the pillar-microwell 204 may be exposed to growth media 504 for incubation. And in some further exemplary methods, the pillar-microwell may be submerged in a conventional microtiter plate 505 that contains growth media 504 for cell culture, as shown in FIG. 6D. Submerging the pillar-microwells 204 in conventional microtiter plates 505 containing cell growth media is an improvement over the current state of the art because it allows for simply changing the growth media without disturbing the cell layers with a microplate washer dispenser.

Figure 8:
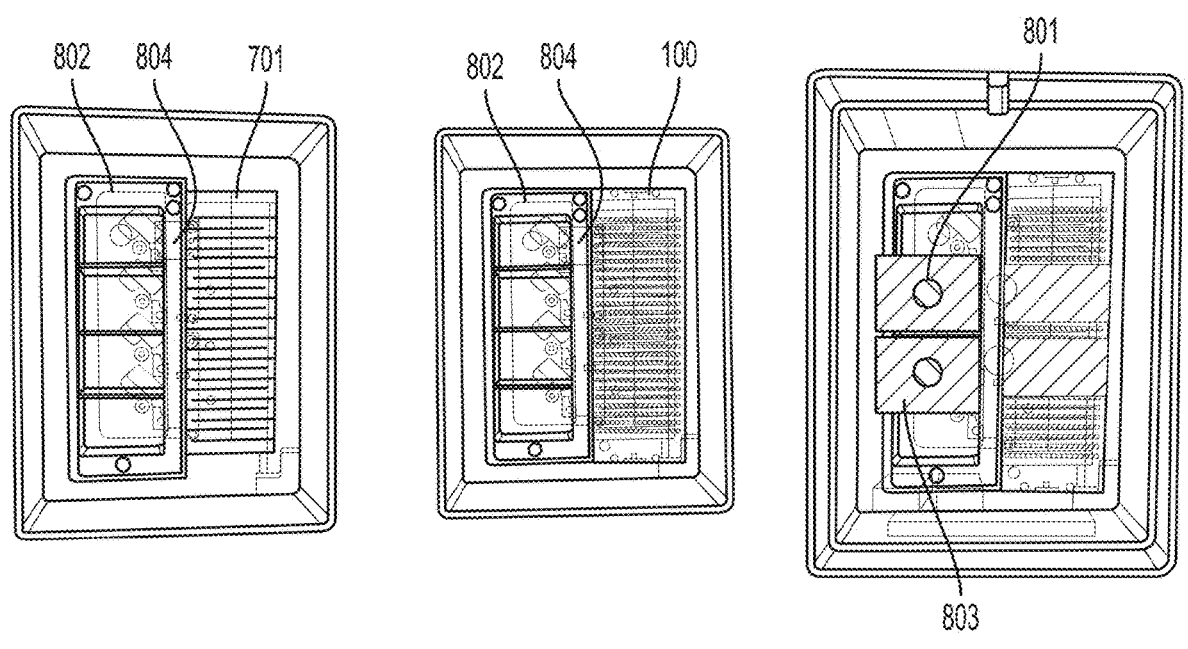
FIG. 8 shows embodiments of perfusion channel chips, micropillar chips, and reservoir chips.
Figure 9A:
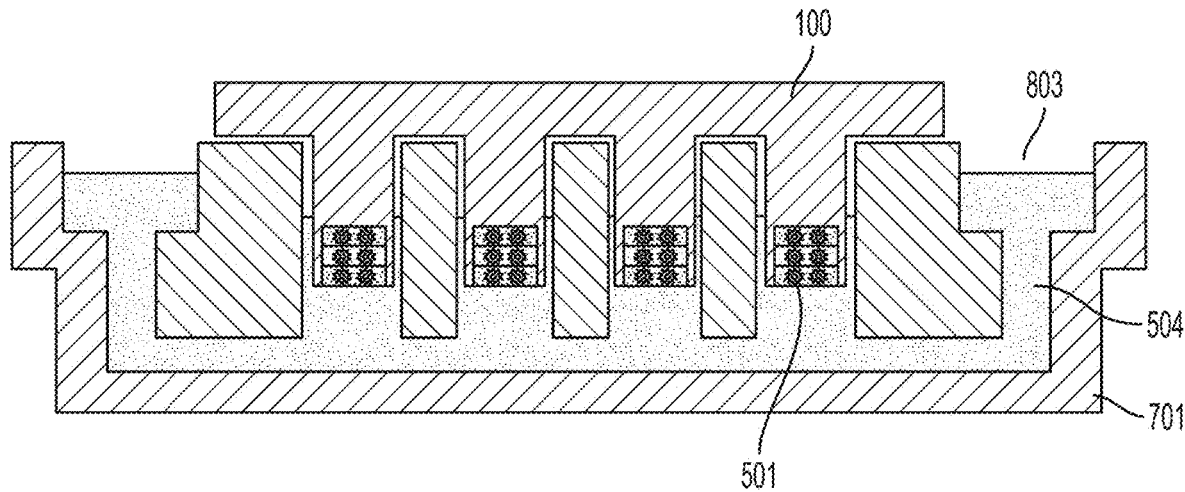
FIG. 9A shows a cross-sectional view of an embodiment of a micropillar chip sandwiched with an embodiment of a perfusion channel chip.
Figure 9B:
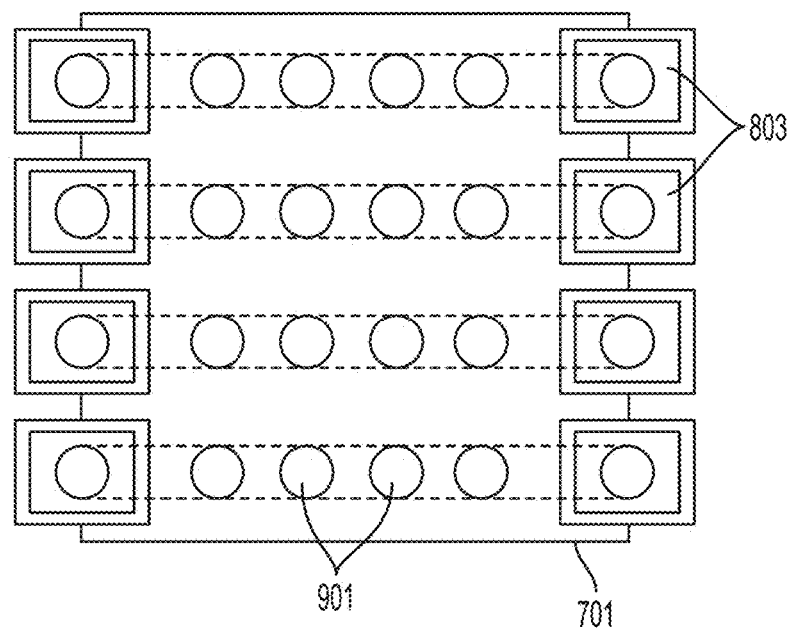
FIG. 9B shows a top view of an embodiment of a perfusion channel chip.

Referring to FIGS. 7-9, in some exemplary methods, the micropillar chip may be incubated by submerging the pillar-microwells 204 in a perfusion channel chip 701 containing growth media 504. This method may, for example, be used for long term cultures and may mimic circulatory systems to study, for example, organ-organ interactions. FIGS. 7A-7D, illustrate an embodiment of a perfusion channel chip 701. The perfusion channel chip may comprise one or more compartments 702 containing one or more channels 703. Further, the perfusion channel chip 701 may separate one or more of the compartments 702 with a porous membrane cassette 704. The one or more compartments 702 may contain growth media 504 containing test compounds, biomolecules, drugs, DNAs, RNAs, proteins, bacteria, viruses, or combinations thereof that may flow through or reside in the one or more channels 703. For example, an embodiment of the perfusion channel chip 701 may contain one compartment for liver co-cultures, one compartment for brain cell co-cultures and a porous membrane cassette 704 simulating the blood brain barrier. As shown in FIGS. 7C and 7D, a micropillar chip 100 containing pillar-microwells 204 or conventional pillars may be sandwiched with the perfusion channel chip 701 so that the contents on the pillar or in the pillar-microwell 204 may be in contact with the growth media 504 in the channel 703. As shown in FIG. 9B, the perfusion channel chip may contain pillar insertion holes 901 through which a pillar or pillar-microwell 204 may be inserted.

Referring to FIG. 8, in some further exemplary embodiments using a perfusion channel chip 701, one or more micropumps 804 may be integrated with the perfusion channel chip to circulate the growth media 504. In some further exemplary embodiments, the growth media may be circulated from reservoirs 803. In some further exemplary embodiments, a reservoir chip 802 that contains reservoir wells 803 for growth media may be integrated with the perfusion channel chip 701. In some further exemplary embodiments, the reservoir chip 802 may include a sample injection hole 801 for dispensing any samples that may be desired, including, but not limited to, cell-staining reagents, test compounds, growth media, biomolecules, drugs, DNAs, RNAs, proteins, bacteria, viruses, or combinations thereof.

Referring to FIGS. 22A and 22B, in some exemplary methods, cells 501 may be dispensed into the lower microwell 402 of a microwell chip by a microarray spotter 502. In some exemplary methods, the cells may be entrapped in a hydrogel, and in some exemplary methods, more than one layer or a mixture of cells may be printed into the lower microwell 402. In some further exemplary embodiments, the lower microwell 402 may be treated with functional polymers for cell spot attachment and hydrogel gelation. Subsequently, the cells may be incubated by dispensing cell growth media 504 into the upper microwell 401.

In some exemplary embodiments, after a mini-bioconstruct is created, at least one biosample may be added. Suitable biosamples may include biomolecules, drugs, DNAs, RNAs, cells, growth factors, extracellular matrices, proteins, viruses, bacteria, or combinations thereof. The at least one biosample may be chosen to mimic a particular biological environment or condition. In some exemplary embodiments, the at least one biosample may be printed directly onto the mini-bioconstruct, whether contained in a pillar-microwell 204 or in a lower microwell 402, using the microarray spotter 502. In some further exemplary embodiments, the at least one biosample may be printed into the wells of a conventional microtiter plate 505 using the microarray spotter; then the pillar-microwells 204 containing mini-bioconstructs may be inserted into the microtiter wells containing biosamples or other mini-bioconstructs.

In some exemplary embodiments where the mini-bioconstruct is created in the inventive microwell plate 104, biosamples or biomolecules may be added by sandwiching the microwell plate with a conventional micropillar chip that has been prepared with at least one biosample or biomolecule. Likewise, in some further exemplary methods, after the cells are incubated and a mini-bioconstruct is created on the inventive micropillar plate 100, at least one biosample or biomolecule may be added by sandwiching the micropillar plate 100 with a conventional microwell plate that has been prepared with at least one biosample or biomolecule.

Figure 17A:
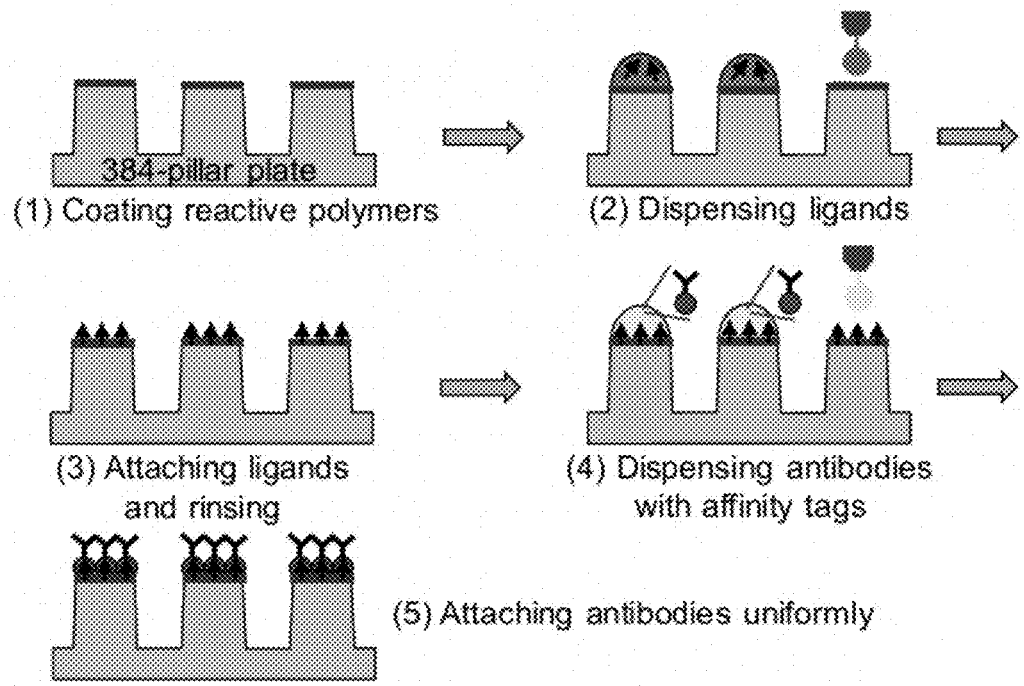
FIG. 17A shows a flowchart demonstrating an embodiment of a method of attaching antibodies to micropillars.

In some exemplary embodiments, in addition to attaching cell spots on the inventive pillar or microwell or conventional pillar or microwell, immobilized antibodies may be attached by using functionalization with reactive polymers for measuring soluble biomarkers. FIG. 17A illustrates an embodiment of this method. In some exemplary embodiments, the surface of the pillar-microwells 204 or conventional pillars may be coated with reactive polymers, including, but not limited to poly(maleic anhydride-alt-1-octadecene (PMA-OD) or poly(styrene-co-maleic anhydride). Then, ligands, for example, poly-L-lysine (PLL), tagged with biotin may be dispensed onto the surface of the coated pillar. Then, after the ligand is immobilized, the pillars may be rinsed to remove any unbound ligands. Next, antibodies with affinity tags, for example, streptavidin or biotin, may be dispensed onto the surface of the pillar so that they interact with the ligands immobilized on the surface of the pillar, achieving attachment of antibodies on the surface of the pillar.

Figure 18A:
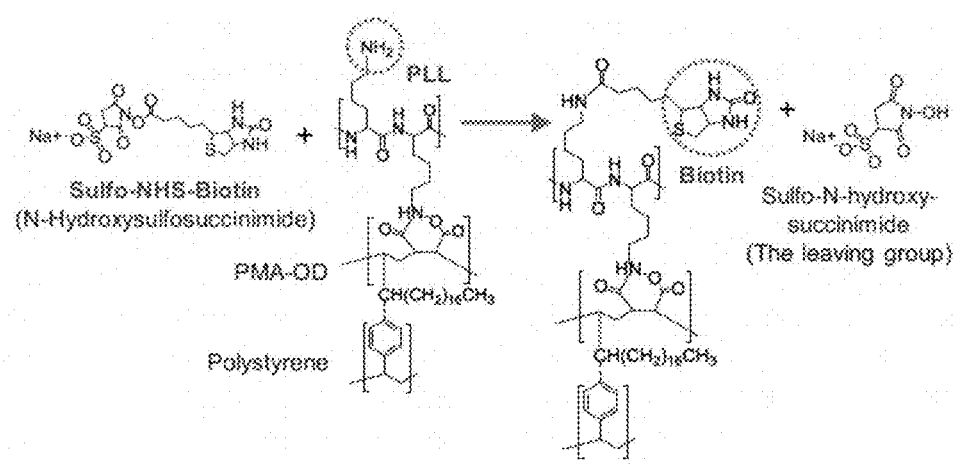
FIG. 18A illustrates the surface chemistry of an embodiment of a method of attaching antibodies to micropillars.
Figure 18B:
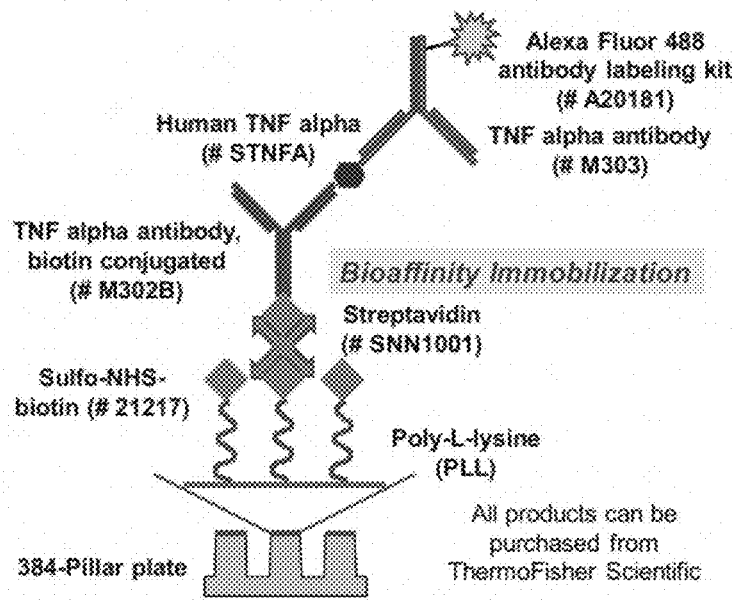
FIG. 18B illustrates the surface chemistry of an embodiment of a method of attaching antibodies to micropillars.
Figure 18C:
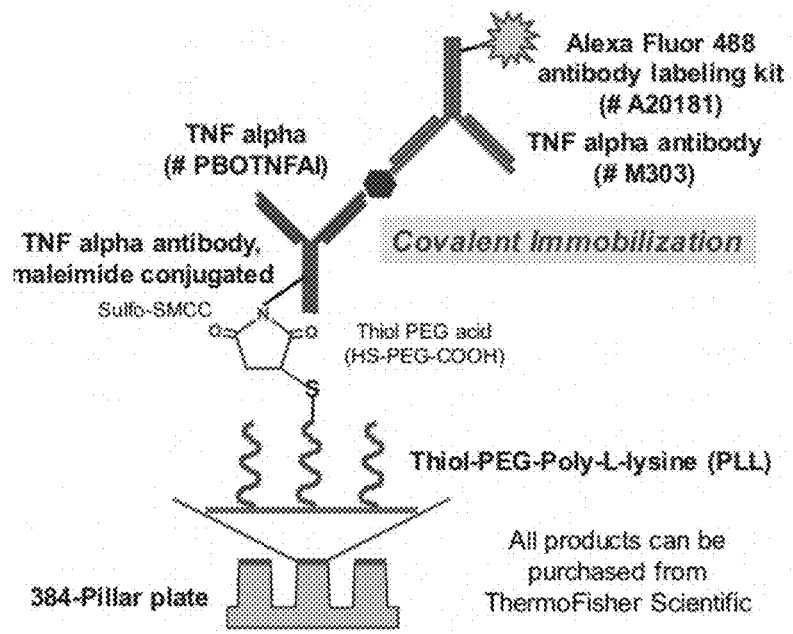

FIGS. 18A-18C illustrate the surface chemistry of an exemplary method of attaching immobilized antibodies to the surface of pillars. FIG. 18A demonstrates surface chemistry of biotin attachment on PLL. FIG. 18B illustrates the surface chemistry of attaching biotin-conjugated antibodies through streptavidin-biotin interactions for sandwich ELISA assays. FIG. 18C illustrates attachment of maleimide-conjugated antibodies through Sulfo-SMCC and thiol reactions for sandwich ELISA assays. Sulfo-SMCC is a water-soluble heterobifunctional protein crosslinker. Sulfo-SMCC protein crosslinker contains an amine reactive Sulfo-NHS ester on one end, which increases its water solubility, and a maleimide functional group that can be utilized to react specifically with cysteines or sulfhydryl (—SH) groups. The maleimide functional group does not readily react with lysine or amino groups (—NH$_2$), thus maleimide-activated conjugates can be readily prepared for later utilization. All products in FIGS. 18B and 18C are commercially available from ThermoFisher Scientific.

Referring to FIG. 19, in some exemplary methods, the inventive or conventional pillars with attached immobilized antibodies may be used to detect secreted biomarkers released by cells by using sandwich ELISA assays. For example, in some embodiments, cells may be entrapped in a hydrogel and dispensed into the pillar-microwell 204 or a conventional pillar. Then, a compound capable of releasing soluble biomarkers (for example, antigens such as cytokines) in the entrapped cells may be dispensed into wells on a well plate. Next, the pillars may be sandwiched with the well plate containing the compound, thus allowing soluble biomarkers to be released by the cells. Then, a pillar plate containing the pillars that has been prepared with attached immobilized antibodies may be sandwiched with the well plate containing the soluble biomarkers. The pillars may be prepared with a variety of antibodies corresponding to different pillars. Then, the pillars may be removed and then sandwiched with wells on a well plate that contain primary antibodies with fluorescent tags, allowing for a sandwich ELISA assay. Sandwich ELISA assay methods are known in the art.

Referring to FIG. 20, in some exemplary methods, soluble biomarkers may also be measured using the inventive pillar chip or conventional pillar chip using immunofluorescent assays in situ. FIG. 20 illustrates an exemplary method for modulating 3D-cultured cells with test compounds and measuring changes in cell surface markers using immunofluorescent assays on a pillar chip. Antibodies with fluorescent tags such as Tyramide signal amplification kits may be used for labeling proteins of interest.

In some further exemplary methods, after the mini-bioconstruct is made, it may be examined by imaging the cells. For example, the mini-bioconstruct may be stained with fluorescent dyes (e.g., calcein AM, ethidium homodimer-1, Hoechst 33342, YO-PRO-1, propidium iodide, TMRM, fluo-4 AM, MCB, a thiol green dye), antibodies with fluorescent tags (e.g., Tyramide signal amplification kit), or recombinant viruses carrying genes for biomarkers (e.g., BactoBac® baculovirus system from ThermoFisher). In some exemplary embodiments, the mini-bioconstruct may be imaged using a high-content imaging scanner, for example. Suitable imaging devices include the S+ Scanner, commercially available from Samsung, GenePix Scanner, commercially available from Molecular Devices, and Cellomics Arrayscan, commercially available from Thermo Fisher. In some further exemplary embodiments, the various layers of cells may be individually targeted for imaging using different Z-focus positions. The small size of the mini-bioconstruct allows for imaging at different Z-focus positions.

Cells and mini-bioconstructs may be stained or otherwise prepared to facilitate imaging, including high-content imaging, before or after the cell-suspension is made. For example, the cells may be stained with fluorescent dyes that indicate certain cellular processes. Examples of dyes and the cellular processes that they may indicate are known in the art, including calcein AM and ethidium homodimer-1 for cell viability and cytotoxicity; Hoechst 33342 for changes in nuclear function; YO-PRO-1/propidium iodide for apoptosis or necrosis; tetramethyl rhodamine methyl ester (TMRM) for mitochondrial membrane potential; fluo-4 AM for intracellular calcium levels; and monochlorobimane (MCB) and thiol green dye for glutathione levels. Cells and mini-bioconstructs may also be stained with recombinant viruses carrying genes for various fluorescent biomarkers. Exemplary recombinant viruses are baculoviruses, for example Bac-to-Bac® baculovirus expression system from ThermoFisher. Other suitable staining methods may be known in the art. Examples of fluorescent biomarkers include blue fluorescent protein (BFP), green fluorescent protein (EGFP), orange fluorescent protein (mOrange), or red fluorescent protein (mCherry).

EXAMPLE 1

Figure 10:
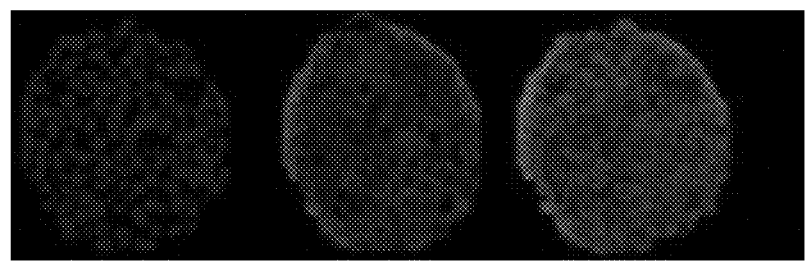
FIG. 10 is an image of a cell-stained mini-bioconstruct.

Mini-bioconstructs were generated by printing several layers of human cell types in photocrosslinkable alginate with extracellular matrices and growth factors onto a 384-pillar plate containing the inventive pillars using a microarray spotter. Hundreds of different biomimetic conditions were provided in the array of inventive pillars. After gelation, the 384-pillar plate was sandwiched with a 384-well plate containing growth media for rapidly testing optimum microenvironments to create human tissue replicates. The mini-bioconstructs were then tested with compounds, stained with fluorescent dyes, and scanned with an automated fluorescent microscope for high-content imaging (HCI) of organ functions and predictive assessment of drug toxicity. FIG. 10 is an example of an image analysis of the mini-bioconstructs.

EXAMPLE 2

Referring to Table 1 below, various inventive pillar structures 204 were tested to analyze the volume of sample that could be loaded into the pillar-microwells depending on sidewall height and number of slits. Inventive pillars of varying sidewall height and number of slits were first coated with 0.01% PMA-OD and dried. Next, 0.05 mg/mL fluorescein isothiocyanate (FITC) dissolved in Dulbecco's phosphate-buffered saline (DPBS) was added in a 384-well plate. The pillar-plate was then sandwiched with the well plate and shaken for 1 hour. Next, the pillar-plate was removed and inserted into a 384-well plate containing 50 μL of DPBS. Then the fluorescent intensities were measured by a plate reader and the FITC volume in the pillar-microwells was back calculated using the calibration curve. The results are shown in Table 1.

taining the varying concentrations of cell suspensions were sandwiched into the 384-well plate and left overnight for incubation. After incubation, the pillars were removed and then sandwiched with a different 384-well plate containing 5 μL of Presto Blue® and 45 μL of growth media for 1, 2, and 3 hours. The fluorescent intensities were then measured by a plate reader to determine cell viability. The calibration curve obtained was y=186.1x+343.0 ($R^2$=0.974), as shown in FIG. 23.

EXAMPLE 4

Figure 13A:
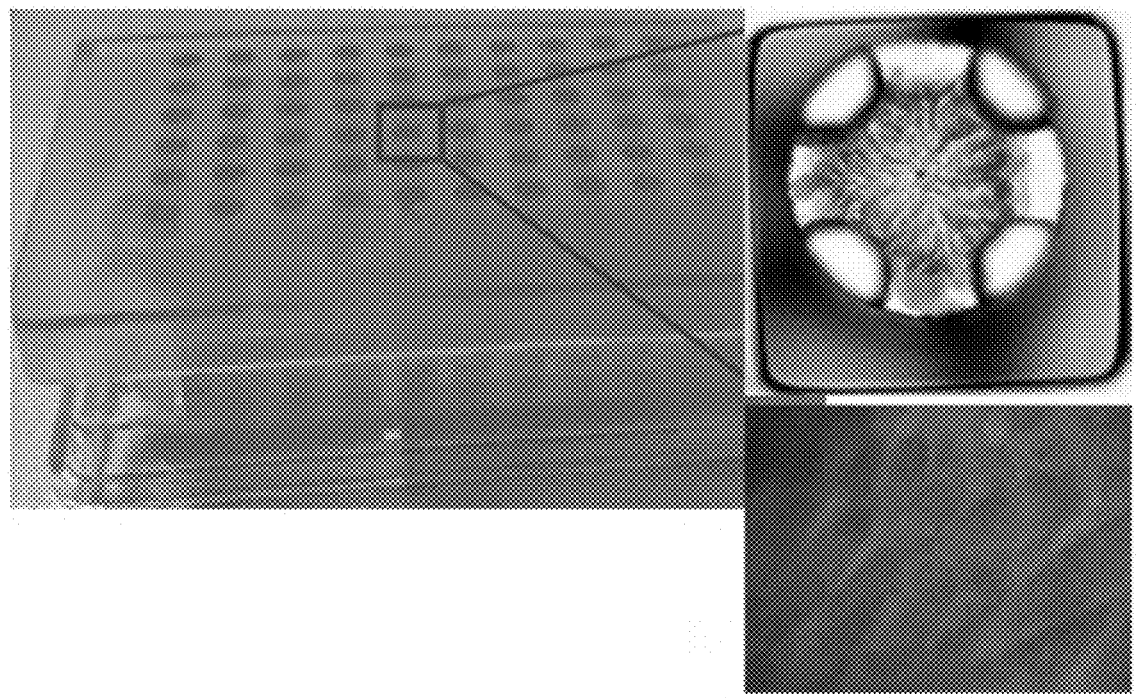
FIG. 13A is an image of Hep3B cells in a micropillar/microwell chip.
Figure 13B:
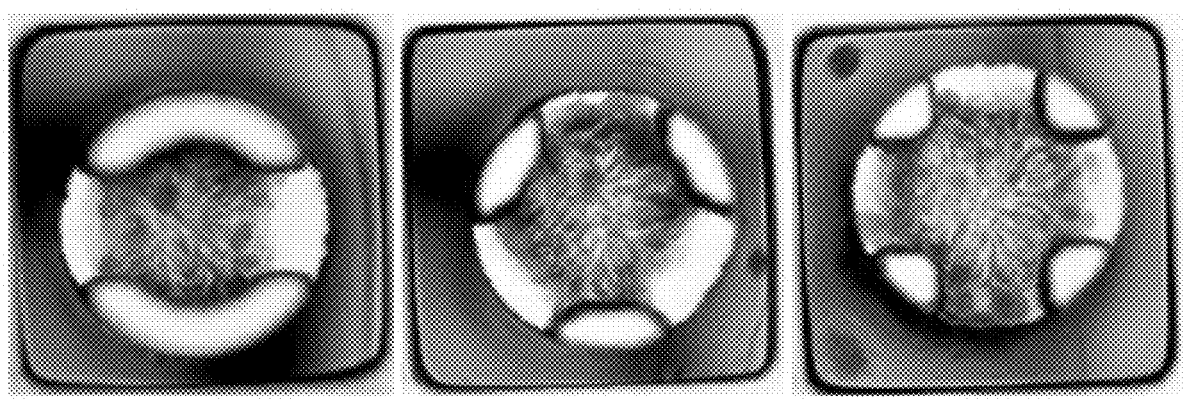
FIG. 13B is images of Hep3B cells in a micropillar/microwell chip.
Figure 14:
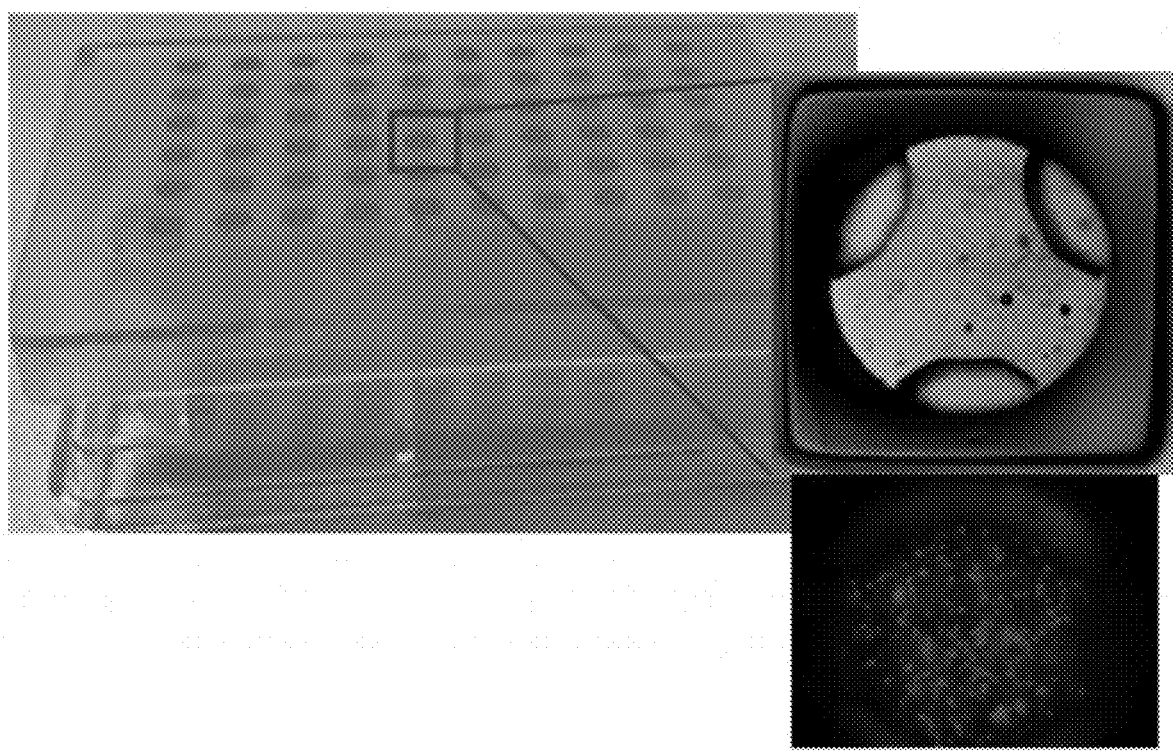
FIG. 14 are images of Hep3B cells in a micropillar/microwell chip.

FIGS. 13A, 13B, and 14 are referenced in Example 4. Various embodiments of the inventive pillars 102 were used to model human liver tumors. Hep3B human hepatoma cells were suspended in alginate and printed on a 60-pillar plate containing pillar-microwells with 2, 3, and 4 slits. FIG. 13A is an image of the 60-pillar plate with bioprinted Hep3B cells in alginate sandwiched onto a 384-well plate containing cell growth media. FIG. 13B is images of bioprinted Hep3B cells in alginate that were cultured over three weeks in pillar-microwells containing 2, 3, and 4 slits. The images show a liver tumor-like organoid culture in the center of the pillar-microwells.

TABLE 1

| | 0.8 mm slit size | | | 0.7 mm slit size | | | 0.6 mm slit size | | |
|---|---|---|---|---|---|---|---|---|---|
| Slits | Sidewall Height (mm) | Mean ± SD | SD/Mean | Sidewall Height (mm) | Mean ± SD | SD/Mean | Sidewall Height (mm) | Mean ± SD | SD/Mean |
| 2 | 1 | 0.278 ± 0.073 | 26.2% | 1 | 0.289 ± 0.037 | 12.8% | 1 | 0.335 ± 0.106 | 31.6% |
| 2 | 1.5 | 0.508 ± 0.083 | 16.3% | 1.5 | 0.554 ± 0.051 | 9.2% | 1.5 | 0.604 ± 0.067 | 11.1% |
| 2 | 2 | 0.603 ± 0.199 | 33.0% | 2 | 0.696 ± 0.081 | 11.6% | 2 | 0.753 ± 0.058 | 7.70% |
| 3 | 1 | 0.270 ± 0.029 | 10.7% | 1 | 0.245 ± 0.049 | 20.0% | 1 | 0.320 ± 0.069 | 21.5% |
| 3 | 1.5 | 0.321 ± 0.104 | 32.4% | 1.5 | 0.412 ± 0.043 | 10.4% | 1.5 | 0.494 ± 0.085 | 17.2% |
| 3 | 2 | 0.379 ± 0.236 | 62.3% | 2 | 0.510 ± 0.115 | 22.5% | 2 | 0.676 ± 0.136 | 20.1% |
| 4 | 1 | 0.242 ± 0.101 | 41.7% | 1 | 0.266 ± 0.082 | 30.8% | 1 | 0.354 ± 0.088 | 24.8% |
| 4 | 1.5 | 0.259 ± 0.134 | 51.7% | 1.5 | 0.369 ± 0.127 | 34.4% | 1.5 | 0.518 ± 0.085 | 16.4% |
| 4 | 2 | 0.267 ± 0.104 | 38.9% | 2 | 0.379 ± 0.110 | 29.0% | 2 | 0.634 ± 0.152 | 24.0% |
| Ctrl | 0 | 0.057 ± 0.029 | 50.8% | 0 | | | 0 | | |

EXAMPLE 3

Figure 11:
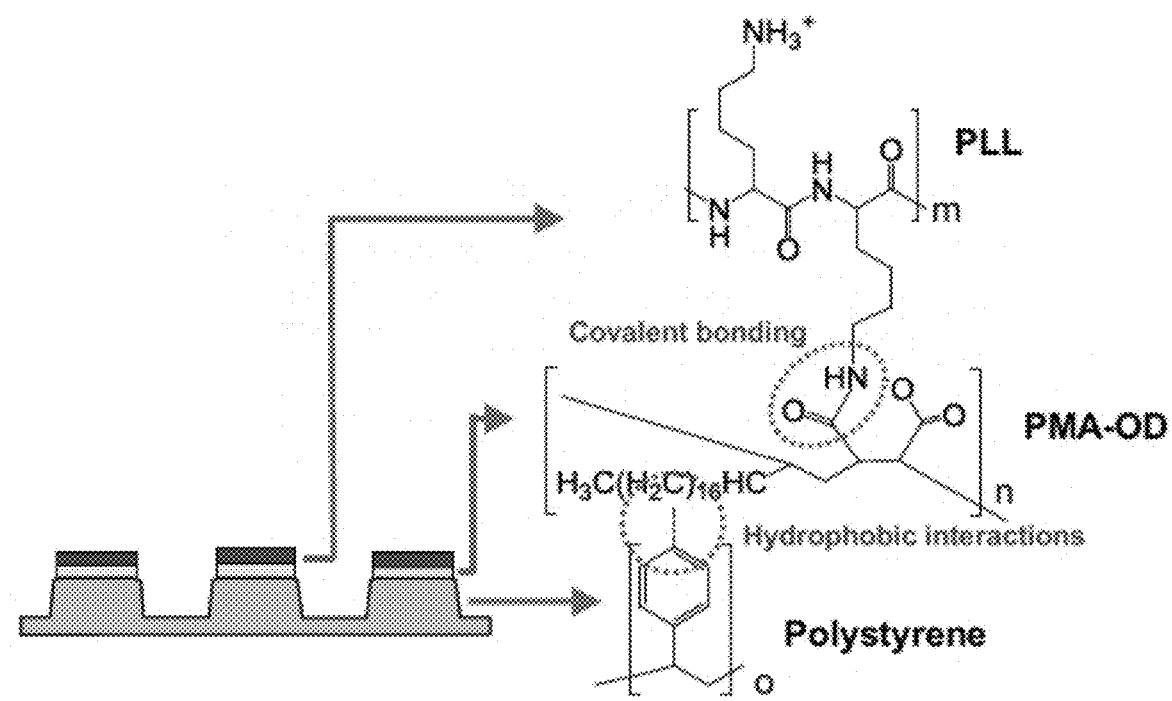
FIG. 11 illustrates the surface chemistry of an embodiment of a functionalized micropillar.
Figure 11:
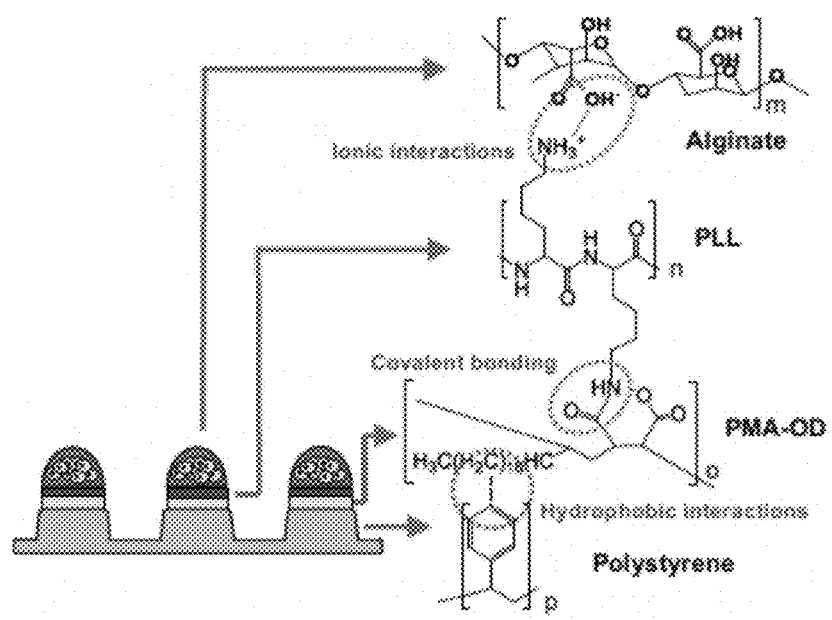
Figure 12:
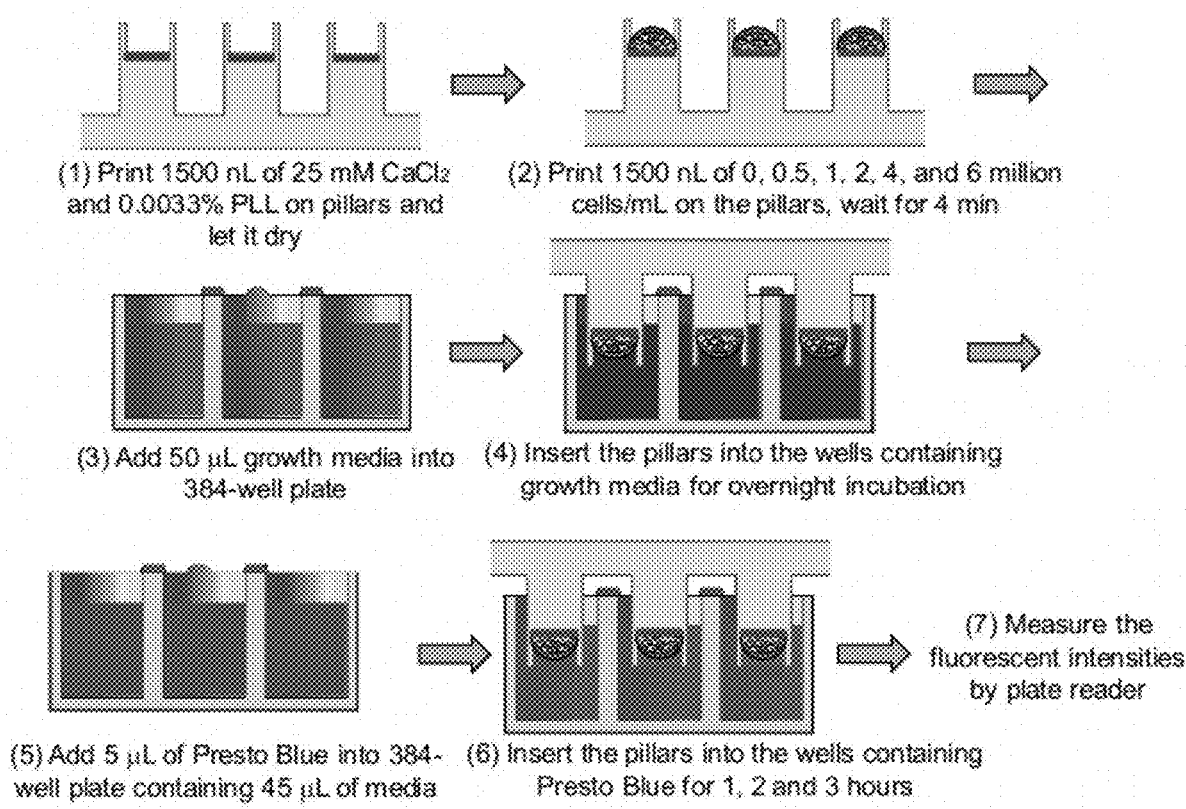
FIG. 12 shows a flowchart demonstrating the method used in Example 3.

FIGS. 11, 12, and 23 are referenced in Example 3. In some embodiments, the surface of the inventive pillar-microwell 204 or microwell 105 may be functionalized to facilitate robust cell-spot attachment. For example, a 384-pillar plate with embodiments of the inventive pillars 102 (1.5 mm sidewall height, 0.6 mm slit size, and 4 slits) was coated with poly(maleic anhydride-alt-1-octadecene) (PMA-OD) to enable covalent attachment of ligands, including poly-L-lysine (PLL). PLL is positively charged, which allows ionic attachment to the negatively charged alginate. 1500 nL of 25 mM $CaCl_2$ and 0.0033% PLL were printed in the pillar-microwells and allowed to dry. Next, 1500 nL of varying concentrations of cell suspensions containing alginate were printed in the pillar-microwells (0, 0.5, 1, 2, 4, and 6 million cells/mL). 50 μL of growth media was then dispensed into the microwells of a 384-well plate. Next, the pillars con- FIG. 14 is an image of color-coded bioprinted human tissues cultured in an embodiment of the inventive pillars. Hep3B cells were transduced with lentivirus carrying a gene for red fluorescent protein (RFP), and the Hep3B cell suspension in alginate was printed on a 60-pillar plate to monitor changes in cell morphology over time. FIG. 14 is an image of the 60-pillar plate containing bioprinted Hep3B cells in alginate infected with lentiviruses carrying a gene for RFP for in situ cell imaging. The red dots indicate live Hep3B cells expressing RFP in the inventive pillar.

EXAMPLE 5

Figure 15:
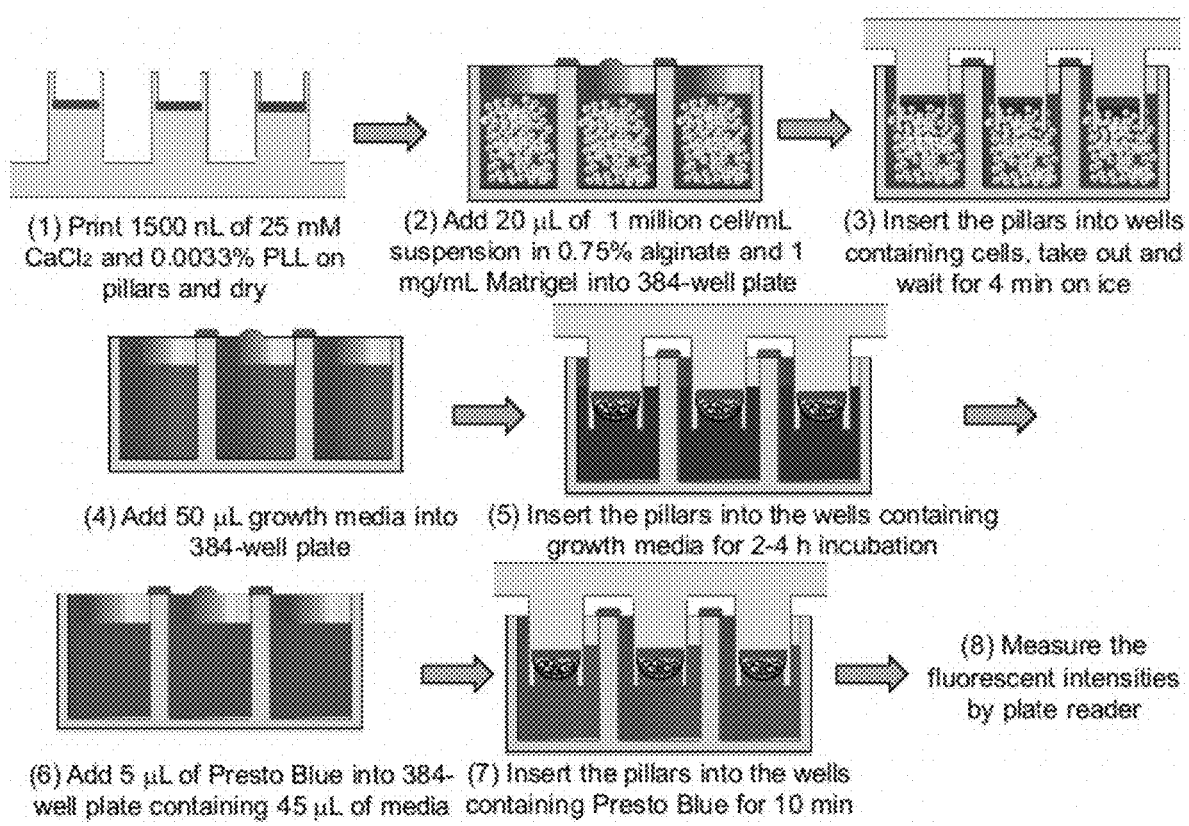
FIG. 15 shows a flowchart demonstrating the method used in Example 5.

FIG. 15 and Table 2 are referenced in Example 5. In some exemplary methods, rather than dispense the cells into pillar-microwells with a microarray spotter, pillar-microwells 204 may be treated with functional polymers and then submerged in a conventional microtiter plate 505 that contains cells suspended in a hydrogel 602, such as alginate. To demonstrate this embodiment, 1500 nL of 25 mM CaCl$_2$ and 0.0033% PLL were printed into the pillar-microwells 204 of various embodiments with varying sidewall 206 height and varying number of slits 207 of the inventive pillars on a 384-pillar plate. Next, 20 μL of 1 million cell/mL suspension in 0.75% alginate and 1 mg/mL Matrigel was added to the wells of a 384-well plate. The pillars were then sandwiched with the well plate containing the cell suspension, taken out, and put on ice for 4 minutes. Next, 50 μL of growth media was added to the wells of a different 384-well plate, and the pillars were then sandwiched with the wells containing the growth media for 2-4 hours for incubation. Next, 5 μL of Presto Blue® and 45 μL of growth media was dispensed into the wells of a different 384-well plate. The pillars were then sandwiched with that well plate containing the Presto Blue® for 10 minutes. Next, the fluorescent intensities were read by a plate reader. Table 2 provides the volumes measured in the various embodiments of the inventive pillar-microwells.

this exemplary method, the surface of a pillar-microwell 204 may be coated with a functional polymer, such as PMA-OD, and crosslinking agents, such as PLL-CaCl$_2$. Next, hydrogels containing chemoattractants (for example, growth factors and extracellular matrices) may be printed into the pillar-microwell 204. Then, cancer cells may be printed (for example, Hep3B cells) on top of the chemoattractant layers. Next, the pillar plate may be sandwiched with a well plate containing growth media for cell culture. Then, the cells in the mini-bioconstructs may be imaged with fluorescent microscopes to assess cancer cell migration in 3D.

FIG. 21 illustrates an exemplary image analysis procedure for quantifying cancer cell migration in 3D using the inventive pillar plate, using Hep3B cells encapsulated in oxidized, methacrylated alginate (OMA). Migration of Hep3B cells in 2% OMA towards the bottom OMA layer containing 1.5 mg/mL of Matrigel was measured by staining the cells with calcein AM and acquiring images using an automated fluorescent microscope and calculating the amount of in-focus

TABLE 2

| | | 0.8 mm slit size | | | 0.7 mm slit size | | | 0.6 mm slit size | |
|---|---|---|---|---|---|---|---|---|---|
| Slits | Sidewall Height (mm) | Mean ± SD | SD/Mean | Sidewall Height (mm) | Mean ± SD | SD/Mean | Sidewall Height (mm) | Mean ± SD | SD/Mean |
| 2 | 1 | 0.650 ± 0.262 | 40.3% | 1 | 0.673 ± 0.085 | 12.6% | 1 | 0.733 ± 0.108 | 14.7% |
| 2 | 1.5 | 0.794 ± 0.416 | 52.4% | 1.5 | 0.597 ± 0.148 | 24.8% | 1.5 | 0.565 ± 0.134 | 23.7% |
| 2 | 2 | 0.903 ± 0.513 | 56.8% | 2 | 0.818 ± 0.179 | 21.9% | 2 | 0.853 ± 0.218 | 25.6% |
| 3 | 1 | 0.602 ± 0.068 | 11.3% | 1 | 0.575 ± 0.304 | 52.9% | 1 | 0.658 ± 0.203 | 30.8% |
| 3 | 1.5 | 0.813 ± 0.191 | 23.5% | 1.5 | 0.769 ± 0.247 | 32.1% | 1.5 | 0.822 ± 0.316 | 38.4% |
| 3 | 2 | 1.056 ± 0.268 | 25.4% | 2 | 1.238 ± 0.218 | 17.6% | 2 | 1.133 ± 0.245 | 21.6% |
| 4 | 1 | 0.729 ± 0.114 | 15.6% | 1 | 0.810 ± 0.371 | 45.8% | 1 | 0.842 ± 0.211 | 25.0% |
| 4 | 1.5 | 0.943 ± 0.228 | 24.2% | 1.5 | 0.873 ± 0.288 | 33.0% | 1.5 | 1.148 ± 0.530 | 46.2% |
| 4 | 2 | 1.213 ± 0.501 | 41.3% | 2 | 1.317 ± 0.387 | 29.4% | 2 | 1.252 ± 0.421 | 33.6% |
| Ctrl | 0 | 0.822 ± 1.549 | 188.4% | 0 | 0 | | | | |

Figure 16:
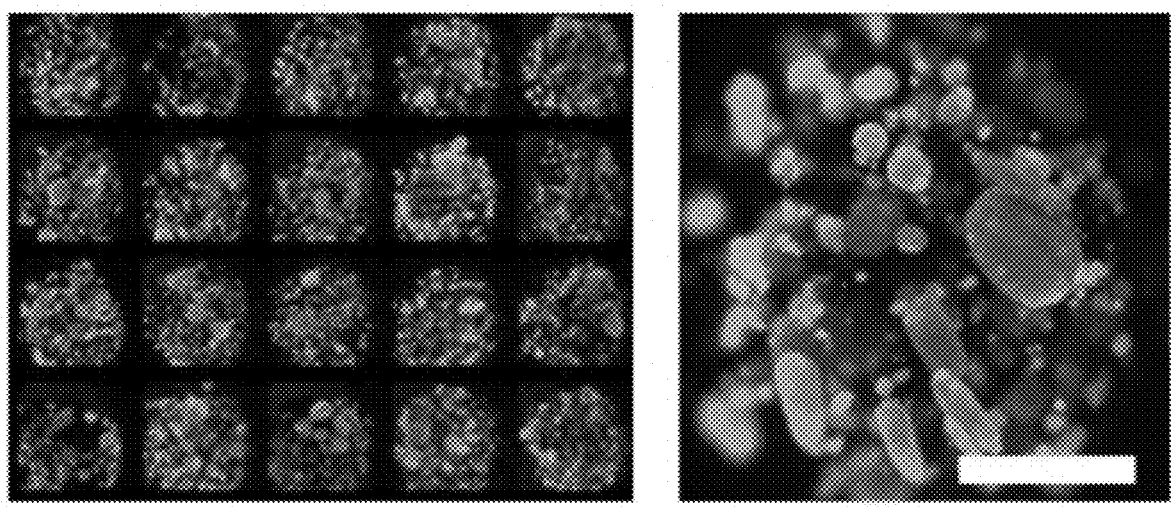
FIG. 16 is images of stained neural progenitor cells.

FIG. 16 is an image of an immortalized human neural progenitor cell line (ReNcell VM from EMD Millipore) encapsulated in a mixture of 0.75% alginate and 1 mg/mL Matrigel on a 384-pillar plate containing embodiments of the inventive pillars. The ReNcell VM cells were encapsulated in a mixture of 0.75% alginate and 1 mg/mL Matrigel, sandwiched with a microwell plate containing growth media, and cultured for two weeks. Each cell spot on the 384-pillar plate initially contained 0.67 million ReNcell VM cells/mL in 1.5 μL of the alginate-Matrigel mixture (1,000 cells/spot). The scale bar in FIG. 16 is 400 μm. The lighter spots indicate live neural stem cell spheroids stained with calcein AM.

EXAMPLE 6

FIG. 21 is referenced in Example 6. In some exemplary methods using the inventive pillars, cells may be printed layer-by-layer in the pillar-microwell, not only to better mimic tissue structures in vivo, but also to monitor changes in cell viability, function, migration, and morphology in situ on the inventive pillar. For example, in one embodiment of images obtained and mean Z-position of cells. Out-of-focus cell images were processed by finite Fourier transform (FFT), band pass filter, and inverse finite Fourier transform (IFFT) to remove out-of-focus cells and obtain in-focus cells. Then, Hue split was performed to obtain green fluorescence from the processed cell images. Next, the mean Z-position of the cells was calculated to assess cancer cell migration in 3D using the equation provided in FIG. 22. This allowed for accurate analysis of in-focus Hep3B cells in the Z-axis. This method may also include infecting the cells with lentiviruses carrying genes for fluorescent proteins, taking images of the infected cells at various Z-positions over time, and observing their migration to chemoattractants in situ.

EXAMPLE 7

Figure 17B:
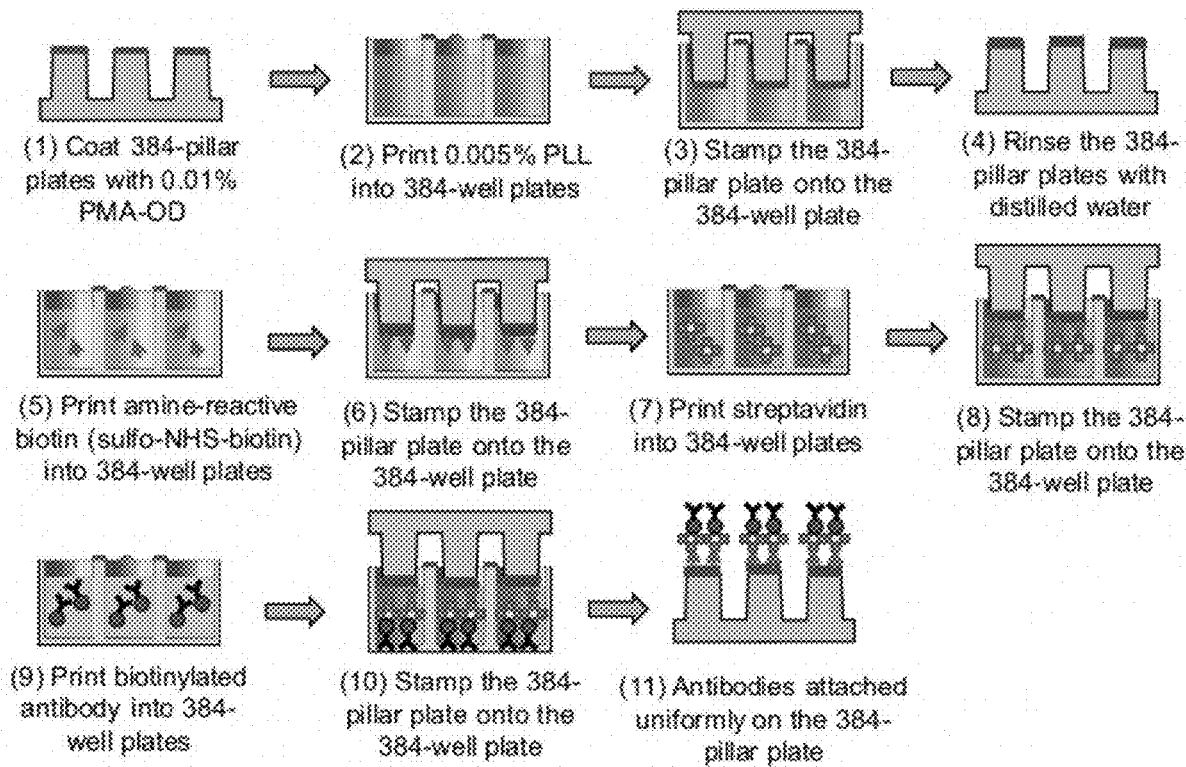
FIG. 17B shows a flowchart demonstrating an embodiment of a method of attaching antibodies to micropillars.

FIG. 17B illustrates an embodiment of a method of uniformly attaching antibodies to the inventive pillar-microwells. First, a pillar plate containing the inventive pillars 102 may be coated with 0.01% PMA-OD. Next, 0.005% PLL may be dispensed into the wells of a well plate. Then, the pillar plate may be sandwiched with the well plate. Next, the pillar plate may be rinsed with distilled water. Then, amine-reactive biotin (sulfo-NHS-biotin) may be dispensed into the wells of a different well plate, and the pillar plate may be sandwiched with this well plate and then removed. Next, streptavidin may be dispensed into the wells of another well plate, and the pillar plate may be sandwiched with this well plate. Next, biotinylated antibody may be dispensed into the wells of another well plate, and the pillar plate may be sandwiched with this well plate.

The inventive aspects have been described with reference to the exemplary embodiments. Modification and alterations will occur to others upon a reading and understanding of this specification. It is intended to include all such modifications and alterations insofar as they come within the scope of the appended claims or the equivalents thereof.

I claim:

1. A pillar plate comprising a plate base and at least one pillar, wherein the at least one pillar comprises a top end, wherein the top end comprises an outer-wall and a base, and wherein the outer-wall has at least one slit that extends through the width of the outer-wall.

2. The pillar plate of claim 1, wherein a bore extends from the top end base through the plate base.

3. The pillar plate of claim 1, wherein the top end comprises at least two slits.

4. A method of creating a miniature multicellular biological construct comprising:
   a) providing a pillar plate comprising a plate base and at least one pillar, wherein the at least one pillar comprises a top end, wherein the top end comprises an outer-wall and a base, and wherein the outer-wall has at least one slit that extends through the width of the outer-wall;
   b) depositing cells into the pillar top end;
   c) submerging the pillar top end in a cell-growth media; and
   d) incubating the cells.

5. The method of claim 4, wherein the cells are deposited into the pillar top end layer-by-layer.

6. The method of claim 4, wherein the cells are deposited into the pillar top end in mixtures.

7. The method of claim 4, wherein the pillar top end is submerged in a perfusion channel chip containing cell-growth media.

8. The method of claim 7, wherein the perfusion channel chip comprises:
   I) at least one channel;
   II) at least one pillar-insertion hole;
   III) at least one membrane cassette; and
   IV) at least one reservoir well.

9. The method of claim 4, wherein the cells are deposited into the pillar top end with a microarray spotter.

10. The method of claim 4, wherein the cells are deposited into the pillar top end by:
    i) submerging the empty pillar top end into a hydrogel containing suspended cells;
    ii) entrapping the hydrogel containing cells within the pillar top end;
    iii) removing the pillar top end from the hydrogel;
    iv) submerging the pillar top end into cell-growth media; and
    v) incubating the cells.

11. The method of claim 4, wherein the cell suspensions are chosen to mimic a human tissue.

12. The method of claim 4, wherein the cell suspensions are chosen to mimic an animal tissue.

13. The method of claim 4, wherein the miniature multicellular biological construct is preconditioned with one or more agents selected from a group containing biomolecules, drugs, DNAs, RNAs, growth factors, extracellular matrices, proteins, viruses, bacteria, cells, growth media, and hydrogels.

14. The method of claim 4, wherein the miniature biological construct is stained with fluorescent dyes, antibodies with fluorescent tags, or recombinant viruses carrying genes for biomarkers.

15. The method of claim 14, wherein the stained miniature biological construct is analyzed at varying depths.

* * * * *